(12) United States Patent
Kock et al.

(10) Patent No.: US 12,305,175 B2
(45) Date of Patent: May 20, 2025

(54) MODIFIED EXCISABLE DAS68416-4 SOYBEAN TRANSGENIC HERBICIDE RESISTANCE LOCUS

(71) Applicant: INARI AGRICULTURE TECHNOLOGY, INC., Cambridge, MA (US)

(72) Inventors: Michael Andreas Kock, Rheinfelden (DE); Joshua L. Price, Cambridge, MA (US); Michael Lee Nuccio, Salem, NH (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 18/057,860

(22) Filed: Nov. 22, 2022

(65) Prior Publication Data

US 2023/0087222 A1 Mar. 23, 2023

Related U.S. Application Data

(63) Continuation of application No. PCT/US2021/043945, filed on Jul. 30, 2021.

(60) Provisional application No. 63/203,137, filed on Jul. 9, 2021, provisional application No. 63/202,569, filed on Jun. 16, 2021, provisional application No. 63/201,030, filed on Apr. 9, 2021, provisional application No. 63/201,029, filed on Apr. 9, 2021, provisional application No. 63/199,951, filed on Feb. 4, 2021, provisional application No. 63/199,949, filed on Feb. 4, 2021, provisional application No. 63/199,930, filed on Feb. 3, 2021, provisional application No. 63/059,860, filed on Jul. 31, 2020, provisional application No. 63/059,813, filed on Jul. 31, 2020, provisional application No. 63/059,916, filed on Jul. 31, 2020, provisional application No. 63/059,963, filed on Jul. 31, 2020.

(51) Int. Cl.

| | |
|---|---|
| C12N 15/82 | (2006.01) |
| A01H 1/02 | (2006.01) |
| A01H 5/10 | (2018.01) |
| A01H 6/46 | (2018.01) |
| A01H 6/48 | (2018.01) |
| A01H 6/54 | (2018.01) |
| C07K 14/41 | (2006.01) |
| C07K 14/415 | (2006.01) |
| C12N 9/22 | (2006.01) |
| C12N 15/11 | (2006.01) |
| C12Q 1/68 | (2018.01) |
| C12Q 1/6834 | (2018.01) |
| C12Q 1/6895 | (2018.01) |

(52) U.S. Cl.
CPC .......... *C12N 15/8201* (2013.01); *A01H 1/02* (2013.01); *A01H 5/10* (2013.01); *A01H 6/4684* (2018.05); *A01H 6/542* (2018.05); *C07K 14/415* (2013.01); *C12N 9/22* (2013.01); *C12N 15/11* (2013.01); *C12N 15/8213* (2013.01); *C12N 15/8286* (2013.01); *C12Q 1/6834* (2013.01); *C12Q 1/6895* (2013.01); *C12N 2310/20* (2017.05); *C12N 2800/80* (2013.01); *C12Q 2600/13* (2013.01); *C12Q 2600/156* (2013.01); *C12Q 2600/158* (2013.01)

(58) Field of Classification Search
CPC . C12N 15/8201; C12N 2310/20; A01H 6/542
See application file for complete search history.

(56) References Cited

U.S. PATENT DOCUMENTS

| | | | |
|---|---|---|---|
| 7,632,985 B2 | 12/2009 | Malven et al. | |
| 8,232,456 B2 | 7/2012 | Long et al. | |
| 8,450,561 B2 | 5/2013 | Beazley et al. | |
| 8,455,720 B2 | 6/2013 | Long et al. | |
| 8,575,434 B2 | 11/2013 | Diehn et al. | |
| 8,680,363 B2 | 3/2014 | Bard et al. | |
| 9,447,428 B2 | 9/2016 | Brinker et al. | |
| 9,540,655 B2 | 1/2017 | Cui et al. | |
| 9,738,904 B2 | 8/2017 | Cui et al. | |
| 9,944,944 B2 * | 4/2018 | Cui | C12Q 1/6895 |
| 11,041,172 B2 | 6/2021 | Cermak | |
| 11,214,811 B1 | 1/2022 | Nuccio et al. | |
| 11,242,534 B1 | 2/2022 | Nuccio et al. | |
| 11,326,177 B2 | 5/2022 | Price et al. | |

(Continued)

FOREIGN PATENT DOCUMENTS

| | | | | |
|---|---|---|---|---|
| WO | WO-2011091311 A2 * | 7/2011 | ............... | A01H 1/02 |
| WO | 2022026375 A1 | 2/2022 | | |

(Continued)

OTHER PUBLICATIONS

Meriam Webster dictionary (Variant Definition & Meaning—Merriam-Webster). https://www.merriam-webster.com/dictionary/variant, accessed May 23, 2023. (Year: 2023).*

(Continued)

*Primary Examiner* — David H Kruse
*Assistant Examiner* — Santosh Sharma
(74) *Attorney, Agent, or Firm* — McKee, Voorhees & Sease, PLC

(57) ABSTRACT

Transgenic INHT27 soybean plants comprising modifications of the DAS68416-4 soybean locus which provide for facile excision of the modified DAS68416-4 transgenic locus or portions thereof, methods of making such plants, and use of such plants to facilitate breeding are disclosed.

12 Claims, 5 Drawing Sheets

Figure 1:
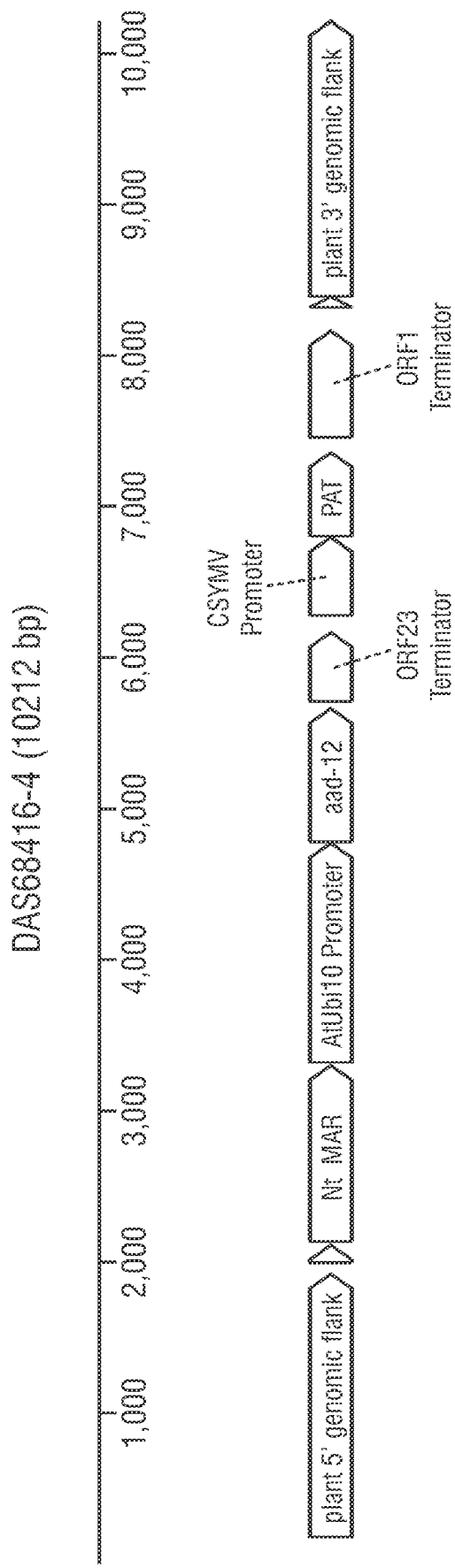

Specification includes a Sequence Listing.

(56) References Cited

U.S. PATENT DOCUMENTS

| | | |
|---|---|---|
| 11,359,210 B2 | 6/2022 | Price et al. |
| 2003/0088081 A1 | 5/2003 | Maliga et al. |
| 2010/0162428 A1 | 6/2010 | Brown et al. |
| 2011/0191899 A1 | 8/2011 | Ainley et al. |
| 2013/0212747 A1 | 8/2013 | Cui et al. |
| 2013/0296170 A1 | 11/2013 | Hanger et al. |
| 2013/0324408 A1 | 12/2013 | Cui et al. |
| 2014/0041083 A1 | 2/2014 | Cui et al. |
| 2015/0059010 A1 | 2/2015 | Cigan et al. |
| 2015/0082478 A1 | 3/2015 | Cigan et al. |
| 2016/0029631 A1 | 2/2016 | Hellwege et al. |
| 2016/0333363 A1 | 11/2016 | Srivastava |
| 2017/0166912 A1 | 6/2017 | Brower-Toland et al. |
| 2018/0163218 A1 | 6/2018 | Corbin et al. |
| 2019/0112614 A1 | 4/2019 | Russell et al. |
| 2019/0136249 A1 | 5/2019 | Sakai et al. |
| 2019/0284644 A1 | 9/2019 | Mackenzie et al. |
| 2019/0320607 A1 | 10/2019 | Christensen et al. |
| 2019/0352655 A1 | 11/2019 | Niu et al. |
| 2020/0157554 A1 | 5/2020 | Cigan et al. |
| 2020/0208172 A1 | 7/2020 | Ikeda et al. |
| 2020/0405649 A1 | 12/2020 | Wang et al. |
| 2022/0030806 A1 | 2/2022 | Price et al. |
| 2022/0030822 A1 | 2/2022 | Nuccio et al. |
| 2022/0033833 A1 | 2/2022 | Gilbertson et al. |
| 2022/0098602 A1 | 3/2022 | Nuccio et al. |
| 2022/0154194 A1 | 5/2022 | Nuccio et al. |
| 2022/0251584 A1 | 8/2022 | Nuccio et al. |
| 2022/0364105 A1 | 11/2022 | Price et al. |
| 2023/0022576 A1 | 1/2023 | Sheva |
| 2023/0077473 A1 | 3/2023 | Price et al. |
| 2023/0078387 A1 | 3/2023 | Kock et al. |
| 2023/0083144 A1 | 3/2023 | Nuccio et al. |
| 2023/0147013 A1 | 5/2023 | Nuccio et al. |
| 2023/0203514 A1 | 6/2023 | Price et al. |
| 2023/0265445 A1 | 8/2023 | Kock et al. |
| 2024/0011042 A1 | 1/2024 | Kock et al. |

FOREIGN PATENT DOCUMENTS

| | | |
|---|---|---|
| WO | 2022026379 A1 | 2/2022 |
| WO | 2022026390 A1 | 2/2022 |
| WO | 2022026395 A2 | 2/2022 |
| WO | 2022026403 A2 | 2/2022 |
| WO | 2022026540 A1 | 2/2022 |
| WO | 2022026801 A1 | 2/2022 |

OTHER PUBLICATIONS

Zhang et al., 2015, Off-target effects in CRISPR/Cas9-mediated genome engineering. Molecular Therapy-Nucleic Acids, 4, e264. (Year: 2015).*

Zhong et al., 2018, Plant genome editing using FnCpf1 and LbCpf1 nucleases at redefined and altered PAM sites. Molecular plant, 11(7), 999-1002. (Year: 2018).*

Li et al., 2018, Expanding the scope of CRISPR/Cpf1-mediated genome editing in rice. Molecular Plant, 11(7), 995-998. (Year: 2018).*

Bagemann et al., 2017, Precise insertion and guided editing of higher plant genomes using Cpf1 CRISPR nucleases. Scientific reports, 7(1), 11606. (Year: 2017).*

Bagemann et al., 2017, Precise insertion and guided editing of higher plant genomes using Cpf1 CRISPR nucleases (Supplementary Data). Scientific reports, 7(1), 11606. (Year: 2017).*

Zhong et al., 2018, Plant genome editing using FnCpf1 and LbCpf1 nucleases at redefined and altered PAM sites (Supplementary Data). Molecular plant, 11(7), 999-1002. (Year: 2018).*

Finnigan et al. 2016. mCAL: a new approach for versatile multiplex action of Cas9 using one sgRNA and loci flanked by a programmed target sequence. G3: Genes, Genomes, Genetics, 6(7), 2147-2156 (reference Publication, see IDS). (Year: 2016).*

Specht et al., 2020, Massively parallel CRISPRi assays reveal concealed thermodynamic determinants of dCas12a binding. Proceedings of the National Academy of Sciences, 117(21), 11274-11282. (Year: 2020).*

Baliga et al., "Investigation of direct repeats, spacers and proteins associated with clustered regularly interspaced short palindromic repeat (CRISPR) system of Vibrio parahaemolyticus," Molecular Genetics and Genomics, Oct. 24, 2018, vol. 294, pp. 253-262.

Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)," PC Code: 006599, U.S. Environmental Protection Agency, Office of Pesticide Programs, Biopesticides and Pollution Prevention Division, Mar. 2009, 175 pages.

Bissler, J.J., "Triplex DNA and human disease," Frontiers in Bioscience, May 1, 2007, vol. 12, pp. 4536-4546.

Bortesi et al., "The CRISPR/Cas9 system for plant genome editing and beyond," Biotechnology Advances, Dec. 20, 2014, vol. 33, Issue 1, pp. 41-52.

Charpentier et al., "Biogenesis pathways of RNA guides in archaeal and bacterial CRISPR-Cas adaptive immunity," FEMS Microbiology Reviews, May 19, 2015, vol. 39, Issue 3, pp. 428-441.

Cho et al., "Nonallelic homologous recombination events responsible for copy number variation within an RNA silencing locus," Plant Direct, vol. 3, Aug. 27, 2019, 16 pages.

Du et al., "Construction of Marker-Free Genetically Modified Maize Using a Heat-Inducible Auto-Excision Vector," Genes, May 17, 2019, vol. 10, No. 374, 17 pages.

Du et al., "Infection of Embryonic Callus with Agrobacterium Enables High-Speed Transformation of Maize," International Journal of Molecular Sciences, Jan. 11, 2019, vol. 20, No. 279, 15 pages.

Finnigan et al., "mCAL: A New Approach for Versatile Multiplex Action of Cas9 Using One sgRNA and Loci Flanked by a Programmed Target Sequence," G3: Genes, Genomes, Genetics, Jul. 1, 2016, vol. 6, pp. 2147-2156.

Gurusaran et al., "RepEx: Repeat extractor for biological sequences," Genomics, Jul. 21, 2013, vol. 102, pp. 403-408.

International Searching Authority in connection with PCT/US21/43897 filed Jul. 30, 2021, "Invitation to Pay Additional Fees And, Where Applicable, Protest Fee," mailed Oct. 27, 2021, 3 pages.

International Searching Authority in connection with PCT/US21/43935 filed Jul. 30, 2021, "Invitation to Pay Additional Fees And, Where Applicable, Protest Fee," mailed Oct. 26, 2021, 3 pages.

International Searching Authority in connection with PCT/US21/43945 filed Jul. 30, 2021, "Invitation to Pay Additional Fees And, Where Applicable, Protest Fee," mailed Oct. 27, 2021, 3 pages.

Kim et al., "CRISPR/Cpf1-mediated DNA-free plant genome editing," Nature Communications, Feb. 16, 2017, vol. 8, Article No. 14406, 7 pages.

Li et al., "Expanding the Scope of CRISPR/Cpf1-Mediated Genome Editing in Rice," Molecular Plant, Jul. 2, 2018, vol. 11, No. 7, pp. 995-998, 14 pages.

Luo et al., "Improperly Terminated, Unpolyadenylated mRNA of Sense Transgenes is Targeted by RDR6-Mediated RNA Silencing in Arabidopsis," The Plant Cell, Mar. 23, 2007, vol. 19, pp. 943-958.

Malzahn et al., "Application of CRISPR-Cas12a temperature sensitivity for improved genome editing in rice, maize, and Arabidopsis," BMC Biology, Jan. 31, 2019, vol. 17, No. 9, 14 pages.

Non-Final Office Action in U.S. Appl. No. 17/248,936, mailed Mar. 25, 2021, 25 pages.

Non-Final Office Action in U.S. Appl. No. 17/249,640, mailed Jun. 29, 2021, 10 pages.

Non-Final Office Action in U.S. Appl. No. 17/302,110, mailed Jun. 29, 2021, 22 pages.

Non-Final Office Action in U.S. Appl. No. 17/302,121, mailed Jul. 8, 2021, 10 pages.

Non-Final Office Action in U.S. Appl. No. 17/302,739, mailed Aug. 3, 2021, 24 pages.

Que et al., "Maize transformation technology development for commercial event generation," Frontiers in Plant Science, Aug. 5, 2014, vol. 5, Article No. 379, 19 pages.

Srivastava et al., "Gene Stacking by recombinases," Plant Biotechnology Journal, Feb. 2016, vol. 14, pp. 471-482.

(56) References Cited

OTHER PUBLICATIONS

Srivastava, et al., "Dual-targeting by CRISPR/Cas9 for precise excision of transgenes from rice genome," Plant Cell Tissue and Organ Culture, Jan. 20, 2017, vol. 129, pp. 153-160.
Ward et al., "Petition for Determination of Nonregulated Status for Insect-Resistant MIR162 Maize," Syngenta Biotechnology, Inc., Aug. 31, 2007, 271 pages.
"What is a CRISPR-Cas system?," CRISPR-CAS++, Universite Paris-Saclay, accessed Nov. 2, 2021. Retrieved from the Internet <URL:https://crisprcas.i2bc.paris-saclay.fr/Home/About>, 2 pages.
Xing et al., "Revealing frequent alternative polyadenylation and widespread low-level transcription read-through of novel plant transcription terminators," Plant Biotechnology Journal, Sep. 2010, vol. 8, pp. 772-782.
Young et al., "CRISPR-Cas9 Editing in Maize: Systematic Evaluation of Off-target Activity and Its Relevance in Crop Improvement," Scientific Reports, Apr. 30, 2019, vol. 9, No. 6729, 11 pages.
Danilo et al., "The DFR locus: A smart landing pad for targeted transgene insertion in tomato," PLoS One, Dec. 6, 2018, vol. 13, No. 12, pp. 1-14.
Gleditzsch et al., "PAM identification by CRISPR-Cas effector complexes: diversified mechanisms and structures," RNA Biology, Apr. 2019, vol. 16, No. 4, pp. 504-517.
International Search Report in PCT/US2021/043161, mailed Jan. 5, 2022, 6 pages.
International Search Report in PCT/US2021/043170, mailed Jan. 5, 2022, 6 pages.
International Search Report in PCT/US2021/043187, mailed Jan. 6, 2022, 6 pages.
International Search Report in PCT/US2021/043192, mailed Jan. 27, 2022, 7 pages.
International Search Report in PCT/US2021/043207, mailed Jan. 27, 2022, 6 pages.
International Search Report in PCT/US2021/043440, mailed Dec. 2, 2021, 3 pages.
International Search Report in PCT/US2021/043468, mailed Nov. 26, 2021, 4 pages.
International Search Report in PCT/US2021/043479, mailed Nov. 23, 2021, 3 pages.
International Search Report in PCT/US2021/043483, mailed Dec. 16, 2021, 3 pages.
International Search Report in PCT/US2021/043496, mailed Dec. 1, 2021, 4 pages.
International Search Report in PCT/US2021/043851, mailed Dec. 30, 2021, 6 pages.
International Search Report in PCT/US2021/043919, mailed Jan. 20, 2022, 8 pages.
International Search Report in PCT/US2021/043933, mailed Dec. 30, 2021, 6 pages.
International Search Report in PCT/US2021/044198, mailed Jan. 19, 2022, 6 pages.
Non-Final Office Action in U.S. Appl. No. 17/302,110, mailed May 24, 2023, 27 pages.
Non-Final Office Action in U.S. Appl. No. 17/650,031, mailed May 26, 2023, 11 pages.
Non-Final Office Action in U.S. Appl. No. 17/680,647, mailed Jun. 23, 2023, 11 pages.
Non-Final Office Action in U.S. Appl. No. 18/057,867, mailed Jun. 7, 2023, 17 pages.
Non-Final Office Action in U.S. Appl. No. 18/058,081, mailed Apr. 11, 2023, 19 pages.
Non-Final Office Action in U.S. Appl. No. 18/058,144, mailed Jun. 7, 2023, 49 pages.
Non-Final Office Action in U.S. Appl. No. 18/058,156, mailed May 19, 2023, 24 pages.
Non-Final Office Action in U.S. Appl. No. 18/058,161, mailed Apr. 11, 2023, 15 pages.
Non-Final Office Action in U.S. Appl. No. 18/162,134, mailed Jun. 21, 2023, 28 pages.
Notice of Allowance in U.S. Appl. No. 17/248,936, mailed Mar. 10, 2022, 7 pages.
Notice of Allowance in U.S. Appl. No. 17/249,640, mailed Sep. 22, 2021, 7 pages.
Notice of Allowance in U.S. Appl. No. 17/302,121, mailed Nov. 15, 2021, 7 pages.
Notice of Allowance in U.S. Appl. No. 17/302,739, mailed Mar. 30, 2022, 7 pages.
Notice of Allowance in U.S. Appl. No. 17/680,647, mailed Apr. 27, 2023, 7 pages.
Rudgers et al., "EXZACTTM Precision Technology: Scientific and Regulatory Advancements in Plant-Genome Editing with ZFNs," NABC, 2014, pp. 113-124.
Shi et al., "ARGOS8 variants generated by CRISPR-Cas9 improve maize grain yield under field drought stress conditions," Plant Biotechnology Journal, Feb. 2017, vol. 15, pp. 207-216.
Yau et al.,"Less is more: strategies to remove marker genes from transgenic plants," BMC Biotechnology, Apr. 2013, vol. 13, No. 36, pp. 1-23.
GenBank Accession No. CP0049894, "Arachis ipaensis cultivar K30076 chromosome 03," Jun. 3, 2020, https://www.ncbi.nlm.nih.gov/nuccore/CP049894, 2 pages.
International Search Report and Written Opinion in PCT/US2021/043897, mailed Feb. 10, 2022, 12 pages.
International Search Report and Written Opinion in PCT/US2021/043935, mailed Jan. 6, 2022, 13 pages.
International Search Report and Written Opinion in PCT/US2021/043945, mailed Jan. 21, 2022, 15 pages.
Li et al. Expanding the scope of CRISPR/Cpf1-mediated genome editing in rice; Molecular Plant 11:995-998, 2018, Supplemental Data, p. 1-10.
Ali et al., "Fusion of the Cas9 endonuclease and the VirD2 relaxase facilitates homology-directed repair for precise genome engineering in rice," Communications Biology, vol. 3, Jan. 2020, 13 pages.
Bernabe-Orts et al., "Assessment of Cas12a-mediated gene editing efficiency in plants," Plant Biotechnology Journal, vol. 17, No. 10, 2019, pp. 1971-1984.
Cai et al., "Broadening the targetable space: engineering and discovery of PAM-flexible Cas proteins," Trends in Microbiology, May 2024, 4 pages.
Non-Final Office Action in U.S. Appl. No. 17/302,110, mailed Oct. 16, 2024, 24 pages.
Extended European Search Report in EP21849192.6, mailed Aug. 30, 2024, 17 pages.
Lee et al., "Activities and specificities of CRISPR/Cas9 and Cas12a nucleases for targeted mutagenesis in maize," Plant Biotechnology Journal, vol. 17, No. 2, 2019, pp. 362-372.
Non-Final Office Action in U.S. Appl. No. 18/162,134, mailed Sep. 26, 2024, 27 pages.
Wang et al., "Generation of marker-free transgenic rice using CRISPR/Cas9 system controlled by floral specific promoters," Journal of Genetics and Genomics, vol. 46, 2019, pp. 61-64.
"Requirement for Unity of Invention" cited in U.S. Appl. No. 18/007,001, filed Jan. 26, 2023, 8 pages, mailed Jan. 27, 2025.

\* cited by examiner

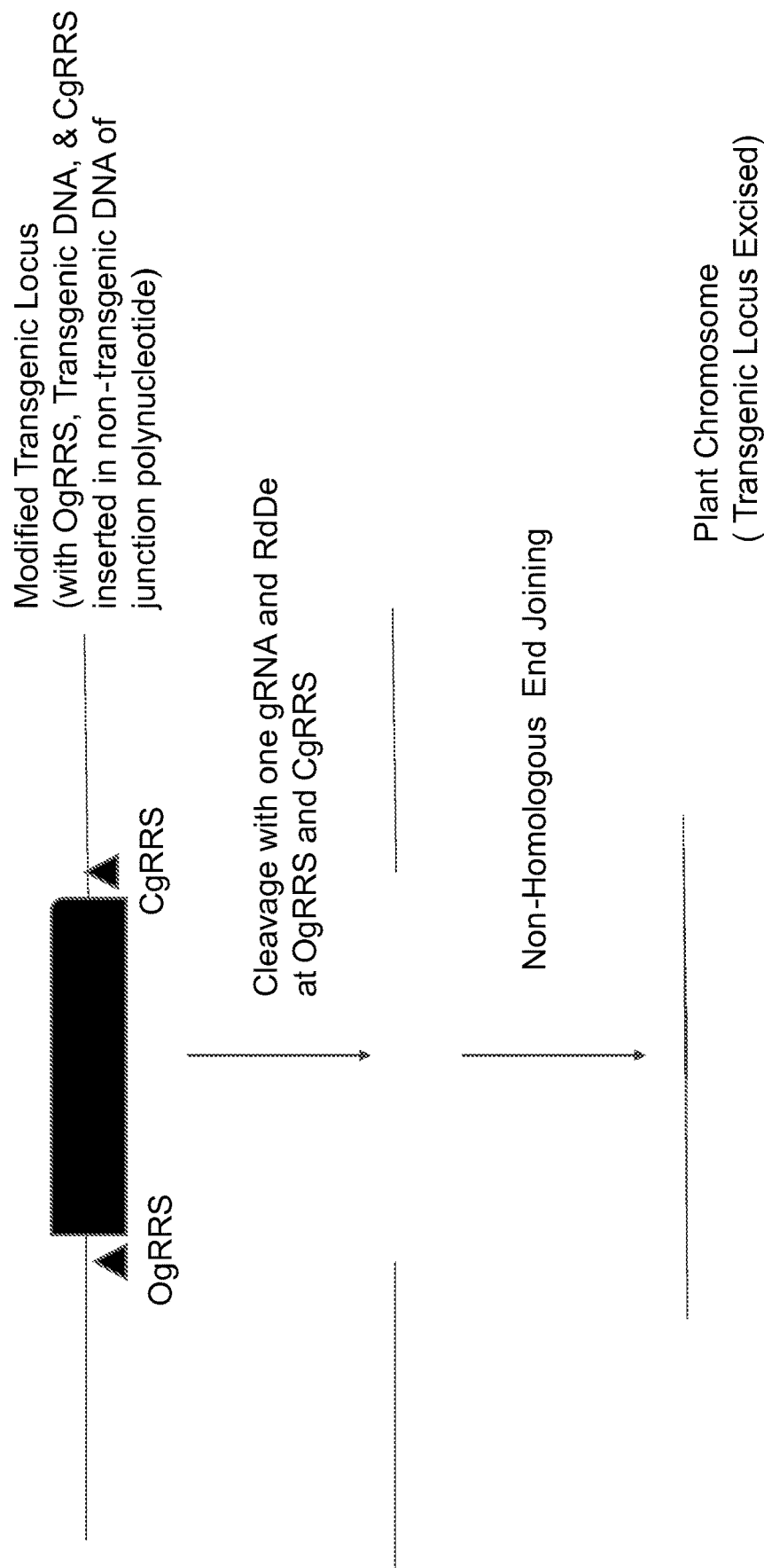

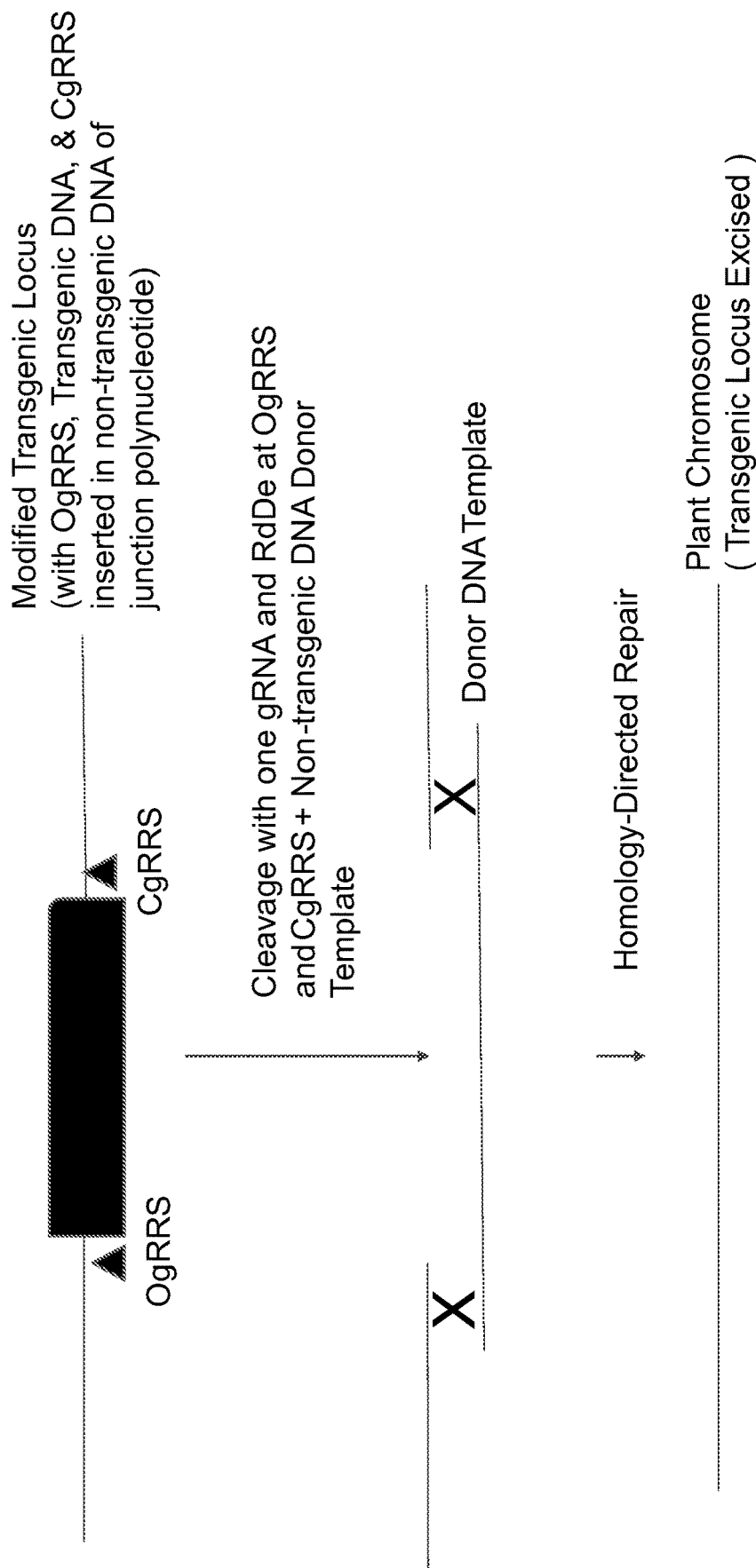

SEQUENCE LISTING

```
Sequence total quantity: 23
SEQ ID NO: 1            moltype = DNA  length = 10212
FEATURE                 Location/Qualifiers
source                  1..10212
                        mol_type = other DNA
                        organism = synthetic construct
SEQUENCE: 1
ctgtcgttgg attcacagaa cattgacgcc agttttcact tcgttatctt tgaattcatt    60
aaaatcgaat ctctcaccta tacccccca tttttctaat ccatcataat caaaattcat    120
aaatgaatca gttaccatta ccataatacc tttttgaaaa tgagtttgaa taatcagtat    180
cttagaaaa ctaattaaga aattaaataa aaaatattta tcatgaagat gagtgtaaga    240
aaaattatga aaagtataac tttatacatt tctataaaat tatttttct tttaatttct    300
taattaatat cctaagtaaa tgagttaata tttatctttc aaaaattctt atagtcgcca    360
attaattttc ccatgcaatg acaacttgtc cgtattctac gtggtaggtt aggctacctg    420
ccgagacaaa ttgccttgag acaaattcaa tagagaaccc ttccaaggga ccattataaa    480
tagagaactt tcattaaccg ataagccaca cccttcaat caaacacaaa cacttgaagt    540
actaagttag tgtgtttgag caaattaact atggcttcgt tttgttctag attgacaatt    600
tgtttggctc tgttttgtcct catatggggg agtgccaatg cacaacttc tacaaacttt    660
tactaccatt catgtccaaa cctcttctcc tctgtgaaat ccacagtgca atctgccata    720
tctaaggaga cccgcatggg tgcttctctc cttgcttgt tcttccacga ttgctttgtc    780
aatgtaattt atttgcacct tctcccactt acatacaaat atgctaagct tacatatagc    840
tcctcttct accacttgca tgcatcatct aattttgttt gaaacaacac ttgttccttt    900
tattatacac atcatcttg ataaaatttt gtcgtgtgca acttttttt agtgtgttaa    960
tcagttctat gatgatacta ttagttaaga aattttaatg cacttaataa accatttaa   1020
gtactttaac cgttcaatga tattatatat ttaaagataa taaatatttc tgcttttgtt   1080
tctatattag tgtagttaag aaccttctta cttcttagct agctaaatat taatgagtaa   1140
acattaacaa atgcagggat gtgatggttc aattctattg gatgacacat caagctccac   1200
cggagagaag aacgcaaacc ccaacaggaa ctctgctcgt ggattcgagg ttattgacaa   1260
cattaaatca gccgtggaga aagtgtgtcc aggagttgtt tcctgcgcag atatccttgc   1320
catcgctgcc agagactctg ttcagattgt aagtggtcaa acaaccaaca aaaacacatt   1380
aaactaaatc attaaattgt acatatcaaa attaattacc aatttagtac cacacatgca   1440
attaagaga acatttgtt gattttgatc aatatagctt ggaggcccta catggaatgt   1500
```

```
taaacttgga agaagagacg ctagaactgc tagccaatct gctgctaaca atggcatccc    1560
tgcacccact tcaaacctta accaactcat ctcaagattt agcgctcttg gactttccac    1620
caaggacttg gtcgccttgt ccggtacaaa acatatatca cataattttc caattaatta    1680
catttcaatc atatagtaaa atttctcaat taattaggaa catgagaaac ttatagtcac    1740
acgttctttt gttgaggaat attgcatggt ttaattttgc tttcattagg tggtcacaca    1800
attggacaag caaggtgcac aaacttcaga gcccgcatct acaacgagac caacatagaa    1860
accgcatttg caaggactag gcagcaaagc tgccctagaa catcagggtc aggggacaac    1920
aatctggcac cacttgatct tcaaactcca accagctttg acaactacta cttcaagaac    1980
ctcgttcaga agaagggtct cctccactct gatcagcaac tgttcaacgg tgggtccacc    2040
gactccattg tgcgtggcta cagcaccaac ccgggcacct tctcctctga tttcgccgcc    2100
gccatgatca agatgggaga cattagtcct ctcactggct ccaatggaga aatcaggaag    2160
aattgtagaa ggattaacta atttgattca gtcttgaata ttaagggtcc tacacatacg    2220
caagcaattt aattgtgttt aataagttgt taaaacatgt tttggttgta ttttggattc    2280
ctagtgtagt ttcggtgatc aatgccgtct actttagtgt gttctacttc cctttatttt    2340
tgtttctttt ttacttttc cttaactata ttgtaggaaa aaaaaaatcc tttatcaagc    2400
atttatcaag aacggagttt gcttttaat tttcccttca taacattcca tcagaattca    2460
gttttgcttt tgcttctaaa ttacgttcaa atcagggatg ataatcggtt aggtaatata    2520
tacagtaccc cttgcatagt cacgtttgaa aaatataatc atacttagtt cggtaacaat    2580
ttaaattatc attctcgtaa tcattagcta cttatgcact catatccgta tccgctactt    2640
gctcttgtcg taagtcaata aattaatata aaaaaatact taaaacttgt tacaactaaa    2700
ttaaaaattt attttttaaat cattcaagca ccagtcagca tcatcacacc aaaagttagg    2760
cccgaatagt ttgaaattag aaagctcgca attgaggtct aaaggccaaa ttcgctctta    2820
gccgtacaat attactcacc ggatcctaac cggtgtgatc atgggccgcg attaaaaatc    2880
tcaattatat ttggtctaat ttagtttggt attgagtaaa acaaattcga accaaaccaa    2940
aatataaata tatagttttt atatatatgc ctttaagact ttttatagaa ttttctttaa    3000
aaaatatcta gaaatatttg cgactcttct ggcatgtaat atttcgttaa atatgaagtg    3060
ctccattttt attaacttta aataattggt tgtacgatca cttcttatc aagtgttact    3120
aaaatgcgtc aatctctttg ttcttccata ttcatatgtc aaaacctatc aaaattctta    3180
tatatctttt tcgaatttga agtgaaattt cgataattta aaattaaata gaacatatca    3240
ttatttaggt atcatattga tttttatact taattactaa atttggttaa ctttgaaagt    3300
gtacatcaac gaaaaattag tcaaacgact aaaatataa aatatcatgt gttattaaga    3360
aaattctcct ataagaatat tttaatagat catatgtttg taaaaaaaat taattttttac    3420
taacacatat atttacttat caaaaatttg acaaagtaag attaaaataa tattcatcta    3480
acaaaaaaaa aaccagaaaa tgctgaaaac ccggcaatc cgaaccaatc caaaccgata    3540
tagttggttt ggtttgattt tgatataaac cgaaccaact cggtccattt gcaccctaa    3600
tcataatagc tttaatattt caagatatta ttaagttaac gttgtcaata tcctggaaat    3660
tttgcaaaat gaatcaagcc tatatggctg taatatgaat ttaaaagcag ctcgatgtgg    3720
tggtaatatg taatttactt gattctaaaa aaatatccca agtattaata atttctgcta    3780
ggaagaaggt tagctacgat ttacagcaaa gccagaatac aatgaaccat aaagtgattg    3840
aagctcgaaa tatacgaagg aacaaatatt tttaaaaaaa tacgcaatga cttgaacaa    3900
aagaaagtga tatattttttt gttcttaaac aagcatcccc tctaaagaat ggcagttttc    3960
ctttgcatgt aactattatg ctcccttcgt tacaaaaatt ttggactact attgggaact    4020
tcttctgaaa atagtggcca ccgcttaatt aaggcgcagc atgcccgggc aagcggccgc    4080
acaagtttgt acaaaaaagc aggctccgcg gtgactgact gaaaagcttg tcgacctgca    4140
ggtcaacgga tcaggatatt cttgtttaag atgttgaact ctatggaggt ttgtatgaac    4200
tgatgatcta ggaccggata agttcccttc ttcatagcga acttattcaa agaatgtttt    4260
gtgtatcatt cttgttacat tgttattaat gaaaaaaatat tattggtcat tggactgaac    4320
acgagtgtta aatatggacc aggccccaaa taagatccat tgatatatga attaaataac    4380
aagaataaat cgagtcacca aaccacttgc ctttttttaac gagactttgtt caccaacttg    4440
atacaaaagt cattatccta tgcaaatcaa taatcataca aaaatatcca ataacactaa    4500
aaaattaaaa gaaatggata atttcacaat atgttatacg ataaagaagt tactttttca    4560
agaaattcac tgattttata agcccacttg cattagataa atggcaaaaa aaaacaaaaa    4620
ggaaaagaaa taaagcacga agaattctag aaaatacgaa atacgcttca atgcagtggg    4680
acccacggtt caattattgc caattttcag ctccaccgta tatttaaaaa ataaaacgat    4740
aatgctaaaa aaatataaat cgtaacgatc gttaaatctc aacggctgga tcttatgacg    4800
accgttagaa attgtggttg tcgacgagtc agtaataaac ggcgtcaaag tggttgcagc    4860
cggcacacac gagtcgtgtt tatcaactca aagcacaaat actttcctc aacctaaaaa    4920
taaggcaatt agccaaaaac aactttgcgt gtaaacaacg ctcaatacac gtgtcatttt    4980
attattagct attgcttcac cgccttagct ttctcgtgac ctagtcgtcc tcgtcttttc    5040
ttcttcttct tctataaaac aatacccaaa gcttcttctt cacaattcag atttcaattt    5100
ctcaaaatct taaaaacttt ctctcaattc tctctaccgt gatcaaggta aatttctgtg    5160
ttccttattc tctcaaaatc ttcgattttg ttttcgttcg atcccaattt cgtatatgtt    5220
ctttggttta gattctgtta atcttagatc gaagacgatt ttctgggttt gatcgttaga    5280
tatcatctta attctcgatt agggtttcat aaatatcatc cgatttgttc aaatatttg    5340
agttttgtcg aataattact cttcgatttg tgatttctat ctagatctgg tgttagtttc    5400
tagtttgtgc gatcgaattt gtcgattaat ctgagttttt ctgattaaca gagatctcca    5460
tggctcagac cactctccaa atcacaccca ctggtgccac cttgggtgcc acagtcactg    5520
gtgttcacct tgccacactt gacgatgctg gtttcgctgc cctccatgca gcctggcttc    5580
aacatgcact cttgatcttc cctgggcaac acctcagcaa tgaccaacag attaccttg    5640
ctaaacgctt tggagcaatt gagaggattg gcggaggtga cattgttgcc atatccaatg    5700
tcaaggcaga tggcacagtg cgccagcact ctcctgctga gtgggatgac atgatgaagg    5760
tcattgtggg caacatggcc tggcacgccg actcaaccta catgccagtc atggctcaag    5820
gagctgtgtt cagcgcagaa gttgtcccag cagttgggga cagaacctgc tttgctgaca    5880
tgaggcgcac ctacgatgcc cttgatgagg caacccctga tggttcac caaaggtctg    5940
ctcgtcactc ccttgtgtat tctcagagca agttgggaca tgtccaacag gccgggtcag    6000
cctacatagg ttatgcatg gacaccactg caactcctct cagaccattg gtcaaggtgc    6060
atcctgagac tggaaggccc agcctcttga tcggccgcca tgcccatgcc atccctggca    6120
tggatgcagc tgaatcagag cgcttccttg aaggacttgt tgactgggcc tgccaggctc    6180
ccagagtcca tgctcaccaa tgggctgctg gagatgtggt tgtgtgggac aaccgctgtt    6240
```

```
tgctccaccg tgctgagccc tgggatttca agttgccacg tgtgatgtgg cactccagac  6300
tcgctggacg cccagaaact gagggtgctg ccttggtttg agtagttagc ttaatcacct  6360
agagctcggt caccagcata attttatta atgtactaaa ttactgtttt gttaaatgca  6420
attttgcttt ctcgggattt taatatcaaa atctatttag aaatacacaa tattttgttg  6480
caggcttgct ggagaatcga tctgctatca taaaaattac aaaaaaattt tatttgcctc  6540
aattatttta ggattggtat taaggacgct taaattattt gtcgggtcac tacgcatcat  6600
tgtgattgag aagatcagcg atacgaaata ttcgtagtac tatcgataat ttatttgaaa  6660
attcataaga aaagcaaacg ttacatgaat tgatgaaaca atacaaagac agataaagcc  6720
acgcacattt aggatattgg ccgagattac tgaatattga gtaagatcac ggaatttctg  6780
acaggagcat gtcttcaatt cagcccaaat ggcagttgaa atactcaaac cgccccatat  6840
gcaggagcgg atcattcatt gtttgtttgg ttgcctttgc caacatggga gtccaaggtt  6900
gcggccgcgc gccgacccag ctttcttgta caaagtggtt cggccgcctt aattaaattt  6960
aaatgcccgg gcgtttaaac gcggccgctt aattaaggcc ggcctgcagc aaacccagaa  7020
ggtaattatc caagatgtag catcaagaat ccaatgtttta cgggaaaaac tatggaagta  7080
ttatgtaagc tcagcaagaa gcagatcaat atgcggcaca tatgcaacct atgttcaaaa  7140
atgaagaatg tacagataca agatcctata ctgccagaat acgaagaaga atacgtagaa  7200
attgaaaaag aagaaccagg cgaagaaaag aatcttgaag acgtaagcac tgacgacaac  7260
aatgaaaaga agaagataag gtcggtgatt gtgaaagaa catgagggac acatgtaagg  7320
tggaaaatgt aagggcggaa agtaaccttca tcacaaagga atcttatccc ccactactta  7380
tcctttata ttttccgtg tcattttgc ccttgagttt tcctatataa ggaaccaagt  7440
tcggcatttg tgaaaacaag aaaaaatttg gtgtaagcta ttttctttga agtactgagg  7500
atacaacttc agagaaattt gtaagtttgt agatctccat gtctccggag aggagaccag  7560
ttgagattag gccagctaca gcagctgata tggccgcggt ttgtgatatc gttaaccatt  7620
acattgagac gtctacagtg aactttagga cagagccaca aacaccacaa gagtggattg  7680
atgatctaga gaggttgcaa gatagatacc cttggttggt tgctgaggtt gagggtgttg  7740
tggctgtat tgcttacgct gggccctgga aggctaggaa cgcttacgat tggacagttg  7800
agagtactgt ttacgtgtca cataggcatc aaaggttggg cctaggatcc acattgtaca  7860
cacatttgct taagtctatg gaggcgcaag gttttaagtc tgtggttgct gttataggcc  7920
ttccaaacga tccatctgtt aggttgcatg aggctttggg atacacagcc cggggtacat  7980
tgcgcgcagc tggatacaag catggtggat ggcatgatgt tggttttttgg caaagggatt  8040
ttgagttgcc agctcctcca aggccagtta ggccagttac ccagatctga ggtacctga  8100
gcttgagctt atgagcttat gagcttagag ctcggatcca ctagtaacgg ccgccagtgt  8160
gctggaattc gcccttgact agataggcgc ccagatcggc ggcaatagct tcttagcgcc  8220
atcccgggtt gatcctatct gtgttgaaat agttgcggtg ggcaaggctc tctttcagaa  8280
agacagggca ccaaaggaac ccaaggtgag gtgggctatg gctctcagtt ccttgtggaa  8340
gcgcttggtc taaggtgcag aggtgttagc gggatgaagc aaaagtgtcc gattgtaaca  8400
agatatgttg atcctacgta aggatattaa agtatgtatt catcactaat ataatcagtg  8460
tattccaata tgtactacga tttccaatgt ctttattgtc gccgtatgta atcggcgtca  8520
caaaatatc cccggtgact ttcttttaat ccaggatgaa ataatatgtt attataattt  8580
ttgcgatttg gtccgttata ggaattgaag tgtgcttgcg gtcgccacca ctcccatttc  8640
ataattttac atgtatttga aaaataaaaa tttatggtat tcaatttaaa cacgtatact  8700
tgtaaagaat gatatcttga aagaaatata gtttaaatat ttattgataa aataacaagt  8760
caggtattat agtccaagca aaaacataaa tttattgata caagtttaaa ttcagaaata  8820
tttcaataac tgattatatc agctggtaca ttgccgtaga tgaaagactg agtgcgatat  8880
tatggtgtaa tacatagcgg ccgggtttct agtcaccggt taggatccgt ttaaactcga  8940
ggctagcgca tgcacataga cacacacatc atctcattga tgcttggtaa taattgtcat  9000
tagattgttt ttatgcatag atgcactcga aatcagccaa ttttagacaa gtatcaaacg  9060
gatgtgactt cagtacatta aaaacgtccg caatgtgtta ttaagttgtc taagcgtcaa  9120
tattttaatt cttaacaatc aatatttaa ttcttaaact ttattaaatc taacaataaa  9180
ctgtaagaac taattcttaa acttcaataa acaatactgc gttttagtaa ttaaattaat  9240
aatatataga tatagatata taattttgtca acatattctt acctatttt ccattgaaat  9300
atgttagcaa gttcaaaaaa agttttgaca aaaaactcta ctatctttg tttcatttac  9360
tttatgtgag ggatataata gtaatataac atttagttta tttaaagaaa ataaaaagt  9420
taatttctct ttctgccact gatactctat ggtggagaga tccgatgcag tggtggagcc  9480
tggcctcgac acataagtgt gacgacgcag ctgttgagga gatctgattc gacggtgggg  9540
taatgcatgg tggttgacag gttgatgggt ggagaagacg taattgctac cgccgtcaac  9600
ggaggaagga gcaaagatgt ctcgtatgtg aaaattatgc ggttgagatg ccgtttcatt  9660
cccttttaaa aaatcccttg atggttcaa tgcaaattaa aaattgaaaa ataattaat  9720
tgttcaaatt aaagatttag catgaaaaaa aaaacactta attgtgccca tgactccatg  9780
acctgcgtaa cttgggaagg aaaggaattt ttttgctaaa ggaaggcatg ggaagatgag  9840
agaggagaga gaatcagtgg aagtgagaga aattaacttt ttgttttta aaaactaaat  9900
attatattac tattatatat atatatatat atataaaaa gatttttag ctggattctt  9960
gatataaaaa atttctcacc atatttatta ttatatattt ttttgagat ctcaaaaag  10020
gaagttggat ttcttctcaa taactctaaa aaattttcc tattcaaaa aatattttt  10080
atgtctttct caattgatg aataatatct atttaagtat attttattgt gaaatccaca  10140
aaagtgactg ataaatctaa tttaggatct accattagag aaaataaaat aaattcttat  10200
attatatgtg at                                                     10212

SEQ ID NO: 2          moltype = DNA  length = 10205
FEATURE               Location/Qualifiers
source                1..10205
                      mol_type = other DNA
                      organism = synthetic construct
SEQUENCE: 2
ctgtcgttgg attcacagaa cattgacgcc agttttcact tcgttatctt tgaattcatt   60
aaaatcgaat ctctcaccta tacccccca tttttctaat ccatcataat caaaattcat  120
aaatgaatca gttaccatta ccataatacc tttttgaaaa tgagtttgaa taatcagtat  180
ctttagaaaa ctaattaaga aattaaataa aaaatttta tcatgaagat gagtgtaaga  240
aaaattatga aaagtataac tttatacatt tctataaaat tatttttct tttaatttct  300
```

```
taattaatat cctaagtaaa tgagttaata tttatctttc aaaaattctt atagtcgcca    360
attaattttc ccatgcaatg acaacttgtc cgtattctac gtggtaggtt aggctacctg    420
ccgagacaaa ttgccttgag acaaattcaa tagagaaccc ttccaaggga ccattataaa    480
tagagaactt tcattaaccg ataagccaca ccctttcaat caaacacaaa cacttgaagt    540
actaagttag tgtgtttgag caaattaact atggcttcgt tttgttctag attgacaatt    600
tgtttggctc tgtttgtcct catatggggg agtgccaatg cacaactttc tacaaacttt    660
tactaccatt catgtccaaa cctcttctcc tctgtgaaat ccacagtgca atctgccata    720
tctaaggaga cccgcatggg tgcttctctc cttcgcttgt tcttccacga ttgctttgtc    780
aatgtaattt atttgcacct tctcccactt acatacaaat atgctaagct tacatatagc    840
tcctcttttct accacttgca tgcatcatct aattttgttt gaaacaacac ttgttccttt    900
tattatacac atcatctttg ataaaatttt gtcgtgtgca acttttttt agtgtgttaa    960
tcagttctat gatgatacta ttagttaaga aattttaatg cacttaataa accattttaa   1020
gtactttaac cgttcaatga tattatatat ttaaagataa taaatatttc tgcttttgtt   1080
tctatattag tgtagttaag aaccttctta cttcttagct agctaaatat taatgagtaa   1140
acattaacaa atgcagggat gtgatggttc aattctattg gatgacacat caagcttcac   1200
cggagagaag aacgcaaacc ccaacaggaa ctctgctcgt ggattcgagg ttattgacaa   1260
cattaaatca gccgtggaga aagtgtgtcc aggagttgtt tcctgcgcag atatccttgc   1320
catcgctgcc agagactctg ttcagattgt aagtggtcaa acaaccaaca aaaacacatt   1380
aaactaaatc attaaattgt acatatcaaa attaattacc aatttagtac cacacatgca   1440
attaaagaga acattttgtt gattttgatc aatatagctt ggaggcccta catgaatgt    1500
taaacttgga agaagagacg ctagaactgc tagccaatgc gctgctaaca atggcatccc   1560
tgcaccact tcaaaccta accaactcat ctcaagattt agcgctcttg gactttccac    1620
caaggacttg gtcgccttgt ccggtacaaa acatatatca cataatttc caattaatta   1680
catttcaatc atatagtaaa atttctcaat taattaggaa catgagaaac ttatagtcac   1740
acgttctttt gttgaggaat attgcatggt ttaattttgc tttcattagg tggtcacaca   1800
attggacaag caaggtgcac aaacttcaga gcccgcactc acaacgagac caacatagaa   1860
accgcatttg caaggactag gcagcaaagc tgcctagaa catcagggtc aggggacaac   1920
aatctggcac cacttgatct tcaaactcca accagctttg acaactacta cttcaagaac   1980
ctcgttcaga agaagggtct cctccactct gatcagcaac tgttcaacgg tgggtccacc   2040
gactccattg tgcgtggcta cagcaccaac ccgggcaact tctcctctga tttcgccgcc   2100
gccatgatca agatgggaga cattagtcct ctcactggca ccaatggaga atcaggaag    2160
aattgtagaa ggattaacta atttgattca gtcttgaata ttaagggtcc tacacatacg   2220
caagcaattt aattgtgttt aataagttgt taaaacatgt tttggttgta ttttggattc   2280
ctagtgtagt ttcggtgatc aatgccgtct acttagtgt gttctacttc cctttatttt    2340
tgtttctttt ttactttttc cttaactata ttgtaggaaa aaaaaatcc tttatcaagc    2400
atttatcaag aacggagttt gctttttaat tttcccttca taacattcca tcagaattca   2460
gttttgcttt tgcttctaaa ttacgttcaa atcaggatg ataatcggtt aggtaatata    2520
tacagtaccc cttgcatagt cacgtttgaa aaatataatc atacttagtt cggtaacaat   2580
ttaaattatc attctcgtaa tcattagcta cttatgcact catatccgta tccgctcatt   2640
gctcttgtcg taagtcaata aattaatata aaaaaatact taaaacttgt tacaactaaa   2700
ttaaaaattt attttttaaat cattcaagca ccagcatcac accaaaagtt aggcccgaat   2760
agtttgaaat tagaaagctc gcaattgagg tctacaggcc aaattcgctc ttagccgtac   2820
aatattactc accggatcct aaccggtgtg atcatgggcc gcgattaaaa atctcaatta   2880
tatttggtct aatttagttt ggtattgagt aaaacaaatt cgaaccaaac caaaatataa   2940
atatatagtt tttatatata tgcctttaag acttttttata gaattttctt taaaaaaatat   3000
ctagaaatat ttgcgactct tctggcatgt aatatttcgt taaatatgaa gtgctccatt   3060
tttattaact ttaaataatt ggttgtacga tcacttttctt atcaagtgtt actaaaatgc   3120
gtcaatctct ttgttcttcc atattcatat gtcaaaacct atcaaaattc ttatatatct   3180
ttttcgaatt tgaagtgaaa tttcgataat ttaaaattaa atagaacata tcattattta   3240
ggtatcatat tgatttttat acttaattac taaatttggt taactttgaa agtgtacatc   3300
aacgaaaaat tagtcaaacg actaaaataa ataaatatca tgtgttatta agaaaattct   3360
cctataagaa tattttaata gatcatatgt ttgtaaaaaa aattaattttt tactaacaca   3420
tatatttact tatcaaaaat ttgacaaagt aagattaaaa taatattcat ctaacaaaaa   3480
aaaaaccaga aaatgctgaa aacccggcaa aaccgaacca atccaaaccg atatagttgg   3540
tttggtttga ttttgatata aaccgaacca actcggtcca tttgcacccc taatcataat   3600
agctttaata tttcaagata ttattaagtt aacgttgtca atatcctgga aattttgcaa   3660
aatgaatcaa gcctatatgg ctgtaatatg aatttaaaag cagctcgatg tggtggtaat   3720
atgtaattta cttgattcta aaaaaatatc ccaagtatta ataatttctg ctaggaagaa   3780
ggttagctac gatttacagc aaagccagaa tacaatgaac cataaagtga ttgaagctcg   3840
aaatatacga aggaacaaat atttttaaaa aaatacgcaa tgacttggaa caaaagaaag   3900
tgatatattt tttgttctta acaagcatc ccctctaaag aatggcagtt ttcctttgca    3960
tgtaactatt atgctccctt cgttacaaaa attttggact actattggga acttcttctg   4020
aaaatagtgg ccaccgctta attaaggcgc gccatgcccg gcaagcggc cgcacaagtt    4080
tgtacaaaaa agcaggctcc gcggtgactg actgaaaagc ttgtcgacct gcaggtcaac   4140
ggatcaggat attcttgttt aagatgttga actctatgga ggtttgtatg aactgatgat   4200
ctaggaccgg ataagttccc ttcttcatag cgaacttatt caaagaatgt tttgtgtatc   4260
attcttgtta cattgttatt aatgaaaaaa tattattggt cattggactg aacacgagtg   4320
ttaaatatgg accaggcccc aaataagatc cattgatata tgaattaaat aacaagaata   4380
aatcgagtca ccaaaccact tgcctttttt aacgagactt gttcaccaac ttgatacaaa   4440
agtcattatc ctatgcaaat caataatcat acaaaaatat ccaataacac taaaaaatta   4500
aaagaaatgg ataatttcac aatatgttat acgataaaga agttactttt ccaagaaatt   4560
cactgatttt ataagcccac ttgcattaga taaatgcaa aaaaaacaa aaggaaaag     4620
aaataaagca cgaagaattc tagaaaatac gaaatacgct tcaatgcagt gggacccacg   4680
aattattat tgccaatttt cagctccacc gtatatttaa aaataaaac gataatgcta   4740
aaaaaatata aatcgtaacg atcgttaaat ctcaacggct ggatcttatg acgaccgtta   4800
gaaattgtgg ttgtcgacga gtcagtaata aacggcgtca aagtggttgc agccggcaca   4860
cacgagtcgt gtttatcaac tcaaagcaca aatactttc ctcaacctaa aaataaggca   4920
attagccaaa acaacttgg cgtgtaaaca acgctcaata cacgtgtcat tttattatta   4980
gctattgctt caccgcctta gctttctcgt gacctagtcg tcctcgtctt ttcttcttct   5040
```

```
tcttctataa aacaatacccc aaagcttctt cttcacaatt cagatttcaa tttctcaaaa   5100
tcttaaaaac tttctctcaa ttctctctac cgtgatcaag gtaaattctt gtgttccttca   5160
ttctctcaaa atcttcgatt ttgttttcgt tcgatcccaa tttcgtatat gttctttggt   5220
ttagattctg ttaatcttag atcgaagacg attttctggg tttgatcgtt agatatcatc   5280
ttaattctcg attagggttt cataaatatc atccgatttg ttcaaataat ttgagttttg   5340
tcgaataatt actcttcgat ttgtgatttc tatctagatc tggtgttagt ttctagtttg   5400
tgcgatcgaa tttgtcgatt aatctgagtt tttctgatta acagagatct ccatggctca   5460
gaccactctc caaatcacac ccactggtgc caccttgggt gccacagtca ctggtgttca   5520
ccttgccaca cttgacgatg ctggtttcgc tgccctccat gcagcctggc ttcaacatgc   5580
actcttgatc ttccctgggc aacacctcag caatgaccaa cagattacct ttgctaaacg   5640
ctttggagca attgagagga ttggcggagg tgacattgtt gccatatcca atgtcaaggc   5700
agatggcaca gtgcgccagc actctcctgc tgagtgggat gacatgatga aggtcattgt   5760
gggcaacatg gcctggcacg ccgactcaac ctacatgcca gtcatggctc aaggagctgt   5820
gttcagcgca gaagttgtcc cagcagttgg gggcagaacc tgctttgctg acatgagggc   5880
agcctacgat gcccttgatg aggcaacccg tgctcttgtt caccaaaggt ctgctcgtca   5940
ctcccttgtg tattctcaga gcaagttggg acatgtccaa caggccgggt cagcctacat   6000
aggttatggc atggacacca ctgcaactcc tctcagacca ttggtcaagg tgcatcctga   6060
gactggaagg cccagcctct tgatcggccg ccatgcccat gccccctg gcatgatgc     6120
agctgaatca gagcgcttcc ttgaaggact tgttgactgg gcctgccagg ctcccagagt   6180
ccatgctcac caatgggctg ctggagatgt ggttgtgtgg gacaaccgct gtttgctcca   6240
ccgtgctgag ccctgggatt tcaagttgcc acgtgtgatg tggcactcca gactcgctgg   6300
acgcccagaa actgagggtg ctgccttggt tgagtagtt agcttaatca cctagagctc    6360
ggtcaccagc ataattttta ttaatgtact aaattactgt tttgttaaat gcaattttgc   6420
tttctcggga ttttaatatc aaatctatt tagaaataca caatattttg ttgcaggctt    6480
gctggagaat cgatctgcta tcataaaaat tacaaaaaaa ttttatttgc ctcaattatt   6540
ttaggattgg tattaaggac gcttaaatta tttgtcgggt cactacgcat cattgtgatt   6600
gagaagatca gcgatacgaa atattcgtag tactatcgat aatttatttg aaaattcata   6660
agaaaagcaa acgttacatg aattgatgaa acaatacaaa gacagataaa gccacgcaca   6720
tttaggatat tggccgagat tactgaatat tgagtaagat cacggaattt ctgacaggag   6780
catgtcttca attcagccca aatggcagtt gaaatactca aaccgcccca tatgcaggag   6840
cggatcattc attgtttgtt tggttgcctt tgccaacatg ggagtccaag gttgcggccg   6900
cgcgccgacc cagcttttct gtacaaagtg gttgcggccg cttaattaaa tttaaatgcc   6960
cgggcgttta aacgcggccg cttaattaag gccggcctgc agcaaaccca gaaggtaatt   7020
atccaagatg tagcatcaag aatccatgt ttacgggaaa aactatggaa gtattatgta    7080
agctcagcca gaagcagatc aatatgcggc acatatgcaa cctatgttca aaaatgaaga   7140
atgtacagat acaagatcct atactgccag aatacgaaga agaatacgta gaaattgaaa   7200
aagaagaacc aggcgaagaa aagaatcttg aagacgtaag cactgacgac aacaatgaaa   7260
agaagaagat aaggtcggtg attgtgaaag agacatagag gacacatgta aggtggaaaa   7320
tgtaagggcg gaaagtaacc ttatcacaaa ggaatctaa cccccactac ttatccttt     7380
atattttttcc gtgtcatttt tgcccttgag ttttcctata aaggaacca agttcggcat   7440
ttgtgaaaac aagaaaaaat ttggtgtaag ctatttttctt tgaagtactg aggatacaac   7500
ttcagagaaa tttgtaagtt tgtagatctc catgtctccg gagaggagac cagttgagat   7560
taggccagct acagcagctg atatggccgc ggtttgtgat atcgttaacc attacattga   7620
gacgtctaca gtgaacttta ggacagagcc acaaacacca caagagtgga ttgatgatct   7680
agagaggttg caagatagat acccttggtt ggttgctgag gttgagggtg ttgtggctgg   7740
tattgcttac gctgggccct ggaaggctag gaacgcttac gattggacag ttgagagtac   7800
tgtttacgtg tcacataggc atcaaaggtt gggcctagga tccacattgt acacacattt   7860
gcttaagtct atggaggcgc aaggttttaa gtctgtggtt gctgttatag gccttccaaa   7920
cgatccatct gttaggttgc atgaggcttt gggatacaca gccgtgggta cattgcgcgc   7980
agctggatac aagcatggtg gatggcatga tgttggtttt tggcaaaggg atttgagtt    8040
gccagctcct ccaaggccag ttaggccagt tacccagatc tgaggtaccc tgagcttgga   8100
cttatgagct tatgagctta gagctcggat ccactagtaa cggccgccag tgtgctggaa   8160
ttcgcccttg actagatagg cgcccagatc ggcggcaata gcttcttagc gccatcccgg   8220
gttgatccta tctgtgttga aatagttgcg gtgggcaagg ctctctttca gaaagacagg   8280
cggccaaagg aacccaaggt gaggtgggct atggctctca gttcctttgtg gaagcgcttg   8340
gtctaaggtg cagaggtgtt agcgggatga agcaaaagtg tccgattgta acaagatatg   8400
ttgatcctac gtaaggatat taagtatgt attcatcact aatataatca gtgtattcca    8460
atatgtacta cgatttccaa tgtctttatt gtcgccgtat gtaatcggcg tcacaaaata   8520
atccccggtg actttctttt aatccaggat gaaataatat gttattataa tttttgcgat   8580
ttggtccgtt ataggaattg aagtgtgctt gcggtcgcca ccactcccat ttcataattt   8640
tacatgtatt tgaaaaataa aaatttatgg tattcaattt aaacacgtat acttgtaaag   8700
aatgatatct tgaaagaaat atagtttaaa tatttattga taaataaca agtcaggtat    8760
tatagtccaa gcaaaaacat aaatttattg atgcaagttt aaattcagaa atatttcaat   8820
aactgattat atcagctggt acattgccgt agatgaaagca tgctgga tattatggtg     8880
taatacatag cggccgggtt tctagtcacc ggttaggatc cgtttaaact cgaggctagc   8940
gcatgcacat agacacacac atcatctcat tgatgcttgg taataattgt cattagattg   9000
ttttttatgca tagatgcact cgaaatcagc caattttaga caagtatcaa acggatgtga   9060
cttcagtaca ttaaaaacgt ccgcaatgtg ttattaagtt gtctaagcgt caatattta    9120
attcttaaca atcaatattt taattcttaa actttattaa atctaacaat aaactgtaag   9180
aactaattct taaacttcaa taaacaatac tgcgttttag taattaaatt aataatatat   9240
agatatagat atataaattg tcaacatatt cttacctatt tttccattga aatatgttag   9300
caagttcaaa aaagttttg acaaaaaact ctactatctt tgtttcatt tacttttatgt    9360
gagggatata atagtaatat aacatttagt ttattttaaa aaaataaaaa agttaatttc   9420
tctttctgcc actgatactc tatggtggag agatccgatc agctggcctc ggccctgctc   9480
gacacataag tgtgacgacg cagctgttga agagatctga ttcgacggtg gggtaatgca   9540
tggtggttga caggttgatg ggtggagaag acgtaattgc taccgccgtc aacgaggaa    9600
ggagcaaaga tgtctcgtat gtgaaaatta tgcggttgag atgccgtttc attcccttta   9660
aaaaaatccc ttgatggttg caatgcaaat taaaaattga aaaaataatt aattgttcaa   9720
attaaagatt tagcatgaaa aaaaaaacac ttaattgtgc ccatgactcc atgacctgcg   9780
```

```
taacttggga aggaaaggaa ttttttttgct aaaggaaggc atgggaagat gagagaggag   9840
agagaatcag tggaagtgag agaaattaac tttttgtttt ttaaaaacta aatatattat   9900
tactattata tatatatata tatatatata aaagattttt tagctggatt cttgataaa    9960
aaaatttctc accatattta ttattatata ttttttgga gatctcaaaa aaggaagttg   10020
gatttcttct caataactct aaaaaattat tcctatttca aaaaatattt tttatgtctt  10080
tctctaattg atgaataata tctatttaag tatattttat tgtgaaatcc acaaagtga   10140
ctgataaatc taatttagga tctaccatta gagaaaaata aataaattct tatattatat  10200
gtgat                                                              10205

SEQ ID NO: 3           moltype = DNA   length = 10232
FEATURE                Location/Qualifiers
source                 1..10232
                       mol_type = other DNA
                       organism = synthetic construct
SEQUENCE: 3
ctgtcgttgg attcacagaa cattgacgcc agttttcact tcgttatctt tgaattcatt    60
aaaatcgaat ctctcaccta tacccccca tttttctaat ccatcataat caaaattcat    120
aaatgaatca gttaccatta ccataatacc tttttgaaaa tgagtttgaa taatcagtat   180
ctttagaaaa ctaattaaga aattaaataa aaaatattta tcatgaagat gagtgtaaga   240
aaaattatga aaagtataac tttatacatt tctataaaat tatttttct tttaatttct    300
taattaatat cctaagtaaa tgagttaata tttatcttct aaaaattctt atagtcgcca   360
attaattttc ccatgcaatg acaacttgtc cgtattctac gtggtaggtt aggctacctg   420
ccgagacaaa ttgccttgag acaaattcaa tagagaaccc ttccaaggga ccattataaa   480
tagagaactt tcattaaccg ataagccaca ccctttcaat caaacacaaa cacttgaagt   540
actaagttag tgtgtttgag caaattaact atggcttcgt tttgttctag attgacaatt   600
tgtttggctc tgtttgtcct catatggggg agtgccaatg cacaacttct acaaactttt   660
tactaccatt catgtccaaa cctcttctct tctgtgaaat ccacagtgca atctgccata   720
tctaaggaga cccgcatggg tgcttctctc cttcgcttgt tcttccacga ttgctttgtc   780
aatgtaattt atttgcacct tctcccactt acatacaaat atgctaagct tacatatagc   840
tcctctttct accacttgca tgcatcatct aattttgttt gaaacaacac ttgttccttt   900
tattatacac atcatctttg ataaaatttt gtcgtgtgca actttttttt agtgtgttaa   960
tcagttctat gatgatacta ttagttaaga aatttaatg cacttaataa accattttaa   1020
gtactttaac cgttcaatga tattatatat ttaaagataa taaatatttc tgcttttgtt   1080
tctatattag tgtagttaag aaccttctta cttcttagct agctaaatat taatgagtaa   1140
acattaacaa atgcagggat gtgatggttc aattctattg gatgacacat caagcttcac   1200
cggagagaag aacgcaaacc ccaacaggaa ctctgctcgt ggattcgagg ttattgacaa   1260
cattaaatca gccgtggaga aagtgtgtcc aggagttgtt tcctgcgcag atatccttgc   1320
catcgctgcc agagactctg ttcagattgt aagtggtcaa acaaccaaca aaaacacatt   1380
aaactaaatc attaaattgt acatatcaaa attaattacc aattagtac cacacatgca   1440
attaaagaga acattttgtt gattttgatc aatatagctt ggaggccta catggaatgt    1500
taaacttgga agaagagacg ctagaactgc tagccaatct gctgctaaca atggcatccc   1560
tgcacccact tcaaacctta accaactcat ctcaagattt agcgctcttg gactttccac   1620
caaggacttg gtcgccttgt ccggtacaaa acatatatca cataatttc caattaatta    1680
catttcaatc atatagtaaa atttctcaat taattaggaa catgagaaac ttatagtcac   1740
acgttctttt gttgaggaat attgcatggt ttaattttgc tttcattagg tggtcacaca   1800
attggacaag caaggtgcac aaacttcaga gcccgcatct acaacgagac caacatagaa   1860
accgcatttg caaggactag gcagcaaagc tgccctagaa catcagggtc aggggacaac   1920
aatctggcac cacttgatct tcaaactcca accagctttg acaactacta cttcaagaac   1980
ctcgttcaga agaagggtct cctccactct gatcagcaac tgttcaacgg tgggtccacc   2040
gactccattg tgcgtggcta cagcaccaac ccgggcacct tctcctctga tttcgccgcc   2100
gccatgatca agatgggaga cattagtcct ctcactggct ccaatggaga aatcaggaag   2160
aattgtagaa ggattaacta atttgattca gtcttgaata ttaagggtcc tacacatacg   2220
caagcaattt aattgtgttt aataagttgt taaacatgt tttggttgta ttttggattc    2280
ctagtgtagt ttcggtgatc aatgccgtct acttagtgt gttctacttc cctttatttt    2340
tgtttctttt ttacttttc cttaactata ttgtaggaaa aaaaaaatcc ttatcaagc     2400
atttatcaag aacggagttt gcttttttaat tttcccttca taacattcca tcagaattca   2460
gttttgcttt tgcttctaaa ttacgttcaa atcagggatg ataatcggtt aggtaatata   2520
tacagtaccc cttgcatagt cacgtttgaa aaatataatc atacttagtt cggtaacaat   2580
ttaaattatc attctcgtaa tcattagcta ctttatgcact catatccgta tccgctactt   2640
gctcttgtcg taagtcaata aattaatata aaaaaatact taaaacttgt tacaactaaa   2700
ttaaaaattt atttttaaat cattcaagtt tccattgaaa tatgttagca agttccagca   2760
tcatcacacc aaaagttagg cccgaatagt ttgaaattag aaagctcgca attgaggtct   2820
acaggccaaa ttcgctctta gccgtacaat attactcacc ggatcctaac cggtgtgatc   2880
atgggccgcg attaaaaatc tcaattatat ttggtctaat ttagtttggt attgagtaaa   2940
acaaattcga accaaccaa aatataaata tatgttttt atatatatgc ctttaagact     3000
ttttatagaa ttttctttaa aaaatatcta gaaatatttg cgactcttct ggcatgtaat   3060
atttcgttaa atatgaagtg ctccattttt attaacttta aataattggt tgtacgatca   3120
ctttcttatc aagtgttact aaaatgcgtc aatctcttta ttcttccata ttcatatgtc   3180
aaaacctatc aaaaattctta tatatcttt tcgaatttga agtgaaattt cgataattta    3240
aaattaaata gaacatatca ttatttaggt atcatattga ttttatact taattactaa    3300
atttggttaa ctttgaaagt gtacatcaac gaaaaattag tcaaacgact aaaataaata   3360
aatatcatgt gttattaaga aaattctcct ataagaatat tttaatagat catatgtttg   3420
taaaaaaaat taatttttac taacacatat atttacttat caaaaatttg acaaagtaag   3480
attaaaataa tattcatcta acaaaaaaaa aaccagaaaa tgctgaaaac tgccgcaaaac   3540
cgaaccaatc caaaccgata tagttggttt ggtttgattt tgatataaac cgaaccaact   3600
cggtccattt gcacccctaa tcataatagc tttaatattt caagatatta ttaagttaac   3660
gttgtcaata tcctggaaat tttgcaaaat gaatcaagcc tatatggctg taatatgaat   3720
ttaaaagcag ctcgatgtgg tggtaatatg taatttactt gattctaaaa aaatatccca   3780
agtattaata atttctgcta ggaagaaggt tagctacgat ttacagcaaa gccagaatac   3840
```

```
aatgaaccat aaagtgattg aagctcgaaa tatacgaagg aacaaatatt tttaaaaaaa 3900
tacgcaatga cttggaacaa agaaagtgaa tatatttttt gttcttaaac aagcatcccc 3960
tctaaagaat ggcagttttc cttttgcatgt aactattatg ctcccttcgt tacaaaaatt 4020
ttggactact attgggaact tcttctgaaa atagtggcca ccgcttaatt aaggcgcgcc 4080
atgcccgggc aagcggccgc acaagtttgt acaaaaaagc aggctccgcg gtgactgact 4140
gaaaagcttg tcgacctgca ggtcaacgga tcaggatatt cttgtttaag atgttgaact 4200
ctatggaggt ttgtatgaac tgatgatcta ggaccggata agtcccttc ttcatagcga 4260
acttattcaa agaatgtttt gtgtatcatt cttgttacat tgttattaat gaaaaaatat 4320
tattggtcat tggactgaac acgagtgtta aatatgaacc aggccccaaa taagatccat 4380
tgatatatga attaaataac aagaataaat cgagtcacca aaccacttgc cttttttaac 4440
gagacttgtt caccaacttg atacaaaagt cattatccta tgcaaatcaa taatcataca 4500
aaaatatcca ataacactaa aaaattaaaa gaaatggata atttcacaat atgttatacg 4560
ataaagaagt tacttttcca agaaattcac tgatttttata agcccacttg cattagataa 4620
atggcaaaaa aaaacaaaaa ggaaaagaaa taaagcacga agaattctag aaaatacgaa 4680
atacgcttca atgcagtggg acccacggtt caattattgc caattttcag ctccaccgta 4740
tatttaaaaa ataaaacgat aatgctaaaa aaatataaat cgtaacgatc gttaaatctc 4800
aacggctgga tcttatgacg accgttagaa attgtggttg tcgacgagtc agtaataaac 4860
ggcgtcaaag tggttgcagc cggcacacac gagtcgtgct tatcaactca aagcacaaat 4920
acttttcctc aacctaaaaa taaggcaatt agccaaaaac aactttgcgt gtaaacaacg 4980
ctcaatacac gtgtcatttt attattagct attgcttcac cgcctagct ttctcgtgac 5040
ctagtcgtcc tcgtctttc ttcttcttct tctataaaac aatacccaaa gcttcttctt 5100
cacaattcag atttcaattt ctcaaaatct taaaaacttt ctctcaattc tctctaccgt 5160
gatcaaggta aatttctgtg ttccttattc tctcaaaatc ttcgatttttg ttttcgttcg 5220
atcccaattt cgtatatgtt ctttggtttta gattctgtta atcttagatc gaagacgatt 5280
ttctgggttt gatcgttaga tatcatctta attctcgatt agggtttcat aaatatcatc 5340
cgatttgttc aaatattttg agtttttgtcg aataattact cttcgatttg tgatttctat 5400
ctagatctgg tgttagtttc tagtttgtgc gatcgaattt gtcgattaat ctgagttttt 5460
ctgattaaca gagatctcca tggctcagac cactctccaa atcacaccca ctggtgccac 5520
cttgggtgcc acagtcactg tgttcacct tgccacactt gacgatgctg gtttcgctgc 5580
cctccatgca gcctggcttc aacatgcact cttgatcttc cctgggcaac acctcagcaa 5640
tgaccaacag attacctttg ctaaacgctt tggagcaatt gagaggattg gcggaggtga 5700
cattgttgcc atatccaatg tcaaggcaga tggcacagtg cgccagcact ctcctgctga 5760
gtgggatgac atgatgaagg tcattgtggg caacatggcc tggcacgccg actcaaccta 5820
catgccagtc atggctcaag gagctgtgtt cagcgcagaa gttgtcccag cagttggggg 5880
cagaacctgc tttgctgaca tgagggcagc ctacgatgcc cttgatgagg caacccgtgg 5940
tcttgttcac caaaggtctg ctcgtcactc ccttgtgtat tctcagagca agttgggaca 6000
tgtccaacag gccgggtcag cctacatagg ttatggcatg acaccactg caactcctct 6060
cagaccattg gtcaaggtgc atcctgagac tggaaggccc agcctcttga tcggccgcca 6120
tgcccatgcc aatccctggca tggatgcagc tgaatcagca cgcttccttg aaggacttgt 6180
tgactgggcc tgccaggctc ccagagtcca tgctcaccaa tgggctgctg gagatgtggt 6240
tgtgtgggac aaccgctgtt tgctccaccg tgctgagccc tgggatttca agttgccacg 6300
tgtgatgtgg cactccagac tcgctggacg cccagaaact gagggtgctg ccttggtttg 6360
agtagttagc ttaatcacct agagctcggt caccagcata attttatta atgtactaaa 6420
ttactgttttt gttaaatgca attttgcttt ctcgggattt taatatcaaa atctatttag 6480
aaatacacaa tattttgttg caggcttgct ggagaatcga tctgctatca taaaaattac 6540
aaaaaaattt tatttgcctc aattatttta ggattgtgat taaggacgct taaattattt 6600
gtcgggtcac tacgcatcat tgtgattgag aagatcagcg atacgaaata ttcgtagtac 6660
tatcgataat ttatttgaaa attcataaga aaagcaaacg ttacatgaat tgatgaaaca 6720
atacaaagac agataaagcc acgcacattt aggatattgg ccgagattac tgaatattga 6780
gtaagatcac ggaatttctg acaggagcat gtcttcaatt cagcccaaat ggcagttgaa 6840
atactcaaac cgcccatat gcaggagcgg atcattcatt gtttgtttgg ttgccttttga 6900
caacatggga gtccaaggtt gcggccgcgc gccgacccag cttttcttgta caaagtggtt 6960
gcggccgctt aattaaattt aaatgcccgg gcgtttaaac gcggccgctt aattaaggcc 7020
ggcctgcagc aaacccagaa ggtaattatc caagatgtag catcaagaat ccaatgttta 7080
cgggaaaaac tatggaagta ttatgtaagc tcagcaagaa gcagatcaat atgcggcaca 7140
tatgcaacct atgttcaaaa atgaagaatg tacagataca agatcctata ctgccagaat 7200
acgaagaaga atacgtagaa attgaaaaag aagaaccagg cgaagaaaag aatcttgaag 7260
acgtaagcac tgacgacaac aatgaaaaga agaagataag gtcggtgatt gtgaaagaga 7320
catagaggac acatgtaagg tggaaaatgt aagggcggaa agtaaccttta tcacaaagga 7380
atcttatccc ccactactta tccttttata tttttccgtg tcattttgc ccttgagttt 7440
tcctatataa ggaaccaagt tcggcatttg tgaaaacaag aaaaaaatttg gtgtaagcta 7500
ttttctttga agtactgagg atacaacttc agagaaattt gtaagtttgt agatctccat 7560
gtctccggag aggagaccag ttgagattag gccagctaca gcagctgata tggccgcggt 7620
ttgtgatatc gttaaccatt aacttgagac gtctacagtg aactttagga cagagccaca 7680
aacaccacaa gagtgattg atgatctaga gaggttgcaa gatagatacc cttggttggt 7740
tgctgaggtt gagggtgttg tggctggtat tgcttacgct gggccctgga aggctaggaa 7800
cgcttacgat tggacagttg agagtactgt ttacgtgtca cataggcatc aaaggttggg 7860
cctaggatcc acattgtaca cacatttgct taagtctatg gaggcgcaag gttttaagtc 7920
tgtggttgct gttataggcc ttccaaacga tccatcgtt aggttgcatg aggcttttgg 7980
atacacagcc cggggtacat tgcgcgcagc tggatacaag catggtggat ggcatgatgt 8040
tggtttttgg caaagggatt ttgagttgcc agctcctcca aggccagtta ggccagttac 8100
ccagatctga ggtaccctga gcttgagctt atgagcttat gagcttagag ctcggatcca 8160
ctagtaacgg ccgccagtgt gctggaattc gcccttgact agataggcgc ccagatcggc 8220
ggcaatagct tcttagcgcc atcccgggtt gatcctatct gtgttgaaat agttgcggtg 8280
ggcaaggctc tcttcagaa agacaggcgg ccaaaggaac ccaaggtgag gtgggctatg 8340
gctctcagtt ccttgtggaa gcgcttggtc taaggtgcag aggtgttagc gggatgaagc 8400
aaaagtgtcc gattgtaaca agatatgttg atcctacgta aggatattaa agtatgtatt 8460
catcactaat ataatcagtg tattccaata tgtactacga tttccaatgt ctttattgtc 8520
gccgtatgta atcggcgtca caaaataatc cccggtgact ttcttttaat ccaggatgaa 8580
```

```
ataatatgtt attataattt ttgcgatttg gtccgttata ggaattgaag tgtgcttgcg   8640
gtcgccacca ctcccatttc ataatttttac atgtatttga aaaataaaaa tttatggtat   8700
tcaatttaaa cacgtatact tgtaaagaat gatatcttga aagaaatata gtttaaatat   8760
ttattgataa aataacaagt caggtattat agtccaagca aaaacataaa tttattgatg   8820
caagtttaaa ttcagaaata tttcaataac tgattatatc agctggtaca ttgccgtaga   8880
tgaaagactg agtgcgatat tatggtgtaa tacatagcgg ccgggtttct agtcaccggt   8940
taggatccgt ttaaactcga ggctagcgca tgcacataga cacacacatc atctcattga   9000
tgcttggtaa taattgtcat tagattgttt ttatgcatag atgcactcga aatcagccaa   9060
ttttagacaa gtatcaaacg gatgtgactt cagtacatta aaaacgtccg caatgtgtta   9120
ttaagttgtc taagcgtcaa tattttaatt cttaacaatc aatatttttaa ttcttaaact   9180
ttattaaatc taacaataaa ctgtaagaac taattcttaa acttcaataa acaatactgc   9240
gttttagtaa ttaaattaat aatatataga tatagtata taatttgtca acatattctt   9300
acctattttt ccattgaaat atgttagcaa gttcaaaaaa agtttgaca aaaaactcta   9360
ctatcttttg tttcatttac tttatgtgag ggatataata gtaatataac atttagttta   9420
tttaaagaaa ataaaaaagt taatttctct ttctgccact gatactctat ggtggagaga   9480
tccgatgcag tggtggagcc tggcctcgac acataagtgt gacgacgcag ctgttgaaga   9540
gatctgattc gacggtgggg taatgcatgg tggttgacag gttgatgggt ggagaagacg   9600
taattgctac cgccgtcaac ggaggaagga gcaaagatgt ctcgtatgtg aaaattatgc   9660
ggttgagatg ccgtttcatt cccttttaaaa aaatccccttg atggttgcaa tgcaaattaa   9720
aaattgaaaa aataattaat tgttcaaatt aaagatttag catgaaaaaa aaacactta   9780
attgtgccca tgactccatg acctgcgtaa cttgggaagg aaaggaattt ttttgctaaa   9840
ggaaggcatg ggaagatgag agaggaagga gaatcagtgg aagtgagaa aattaacttt   9900
ttgtttttta aaaactaaat attatattac tattatatat atatatatat atatataaaa   9960
gattttttag ctggattctt gatataaaaa atttctcacc atatttatta ttatatttt   10020
ttttggagat ctcaaaaaag gaagttggat ttcttctcaa taactctaaa aaattattcc   10080
tatttcaaaa aatattttt atgtctttct ctaattgatg aataatatct atttaagtat   10140
attttattgt gaaatccaca aaagtgactg ataaatctaa tttaggatct accattagag   10200
aaaaataaat aaaattcttat attatatgtg at                                 10232

SEQ ID NO: 4           moltype = DNA   length = 27
FEATURE                Location/Qualifiers
source                 1..27
                       mol_type = other DNA
                       organism = synthetic construct
SEQUENCE: 4
tttaaatcat tcaagcacca gtcagca                                        27

SEQ ID NO: 5           moltype = DNA   length = 27
FEATURE                Location/Qualifiers
source                 1..27
                       mol_type = other DNA
                       organism = synthetic construct
SEQUENCE: 5
tttatttta aatcattcaa gcaccag                                         27

SEQ ID NO: 6           moltype = DNA   length = 27
FEATURE                Location/Qualifiers
source                 1..27
                       mol_type = other DNA
                       organism = synthetic construct
SEQUENCE: 6
tttggtgtga tgatgctgac tggtgct                                        27

SEQ ID NO: 7           moltype = DNA   length = 27
FEATURE                Location/Qualifiers
source                 1..27
                       mol_type = other DNA
                       organism = synthetic construct
SEQUENCE: 7
tttccattga aatatgttag caagttc                                        27

SEQ ID NO: 8           moltype = DNA   length = 67
FEATURE                Location/Qualifiers
source                 1..67
                       mol_type = other DNA
                       organism = synthetic construct
SEQUENCE: 8
aaaatttatt tttaaatcat tcaagcacca gtttccattg aaatatgtta gcaagttcca   60
tcacacc                                                             67

SEQ ID NO: 9           moltype = DNA   length = 67
FEATURE                Location/Qualifiers
source                 1..67
                       mol_type = other DNA
                       organism = synthetic construct
SEQUENCE: 9
aaattaaaaa tttattttta aatcattcaa gttccattg aaatatgtta gcaagttcca   60
gcatcat                                                             67
```

| SEQ ID NO: 10 | moltype = DNA length = 67 |
| --- | --- |
| FEATURE | Location/Qualifiers |
| source | 1..67 |
| | mol_type = other DNA |
| | organism = synthetic construct |

SEQUENCE: 10
```
gggcctaact tttggtgtga tgatgctgac ttttccattg aaatatgtta gcaagttcga   60
atgattt                                                             67
```

| SEQ ID NO: 11 | moltype = DNA length = 1127 |
| --- | --- |
| FEATURE | Location/Qualifiers |
| source | 1..1127 |
| | mol_type = other DNA |
| | organism = synthetic construct |

SEQUENCE: 11
```
gattcagtct tgaatattaa gggtcctaca catacgcaag caatttaatt gtgtttaata    60
agttgttaaa acatgttttg gttgtatttt ggattcctag tgtagtttcg gtgatcaatg   120
ccgtctactt tagtgtgttc tacttcccctt tattttgtt tcttttttac ttttccttaa   180
actatattgt aggaaaaaaa aaatccttta tcaagcattt atcaagaacg gagtttgctt   240
tttaatttc ccttcataac attccatcag aattcagttt tgcttttgct tctaaattac   300
gttcaaatca gggatgataa tcggttaggt aatatataca gtaccccttg catagtcacg   360
tttgaaaaat ataatcatac ttagttcggt aacaattgaa attatcattc tcgtaatcat   420
tagctactta tgcactcata tccgtatccg ctacttgctc ttgtcgtaag tcaataaatt   480
aatataaaaa aatacttaaa acttgttaca actaaattaa aaatttattt ttaaatcatt   540
caagcaccag tttccattga aatatgttag caagttccat cacaccaaaa gttaggcccg   600
aatagtttga aattagaaag ctcgcaattg aggtctacag gccaaattcg ctcttagccg   660
tacaatatta ctcaccggat cctaaccggt gtgatcatgg gccgcgatta aaaatctcaa   720
ttatatttgg tctaatttag tttggtattg agtaaaacaa attcgaacca accaaaata   780
taaatatata gttttttatat atatgccttt aagactttt atagaatttt ctttaaaaaa   840
tatctagaaa tatttgcgac tcttctggca tgtaatattt cgttaaatat gaagtgctcc   900
attttattta actttaaata attggttgta cgatcacttt cttatcaagt gttactaaaa   960
tgcgtcaatc tctttgttct tccatattca tatgtcaaaa cctatcaaaa ttcttatata  1020
tcttttcga atttgaagtg aaatttcgat aatttaaaat taaatagaac atatcattat  1080
ttaggtatca tattgatttt tatacttaat tactaaattt ggttaac                1127
```

| SEQ ID NO: 12 | moltype = DNA length = 1378 |
| --- | --- |
| FEATURE | Location/Qualifiers |
| source | 1..1378 |
| | mol_type = other DNA |
| | organism = synthetic construct |

SEQUENCE: 12
```
ccaacccggg caccttctcc tctgatttcg ccgccgccat gatcaagatg ggagacatta    60
gtcctctcac tggctccaat ggagaaatca ggaagaattg tagaaggatt aactaatttg   120
attcagtctt gaatattaag ggtcctacac atacgcaagc aatttaattg tgtttaataa   180
gttgttaaaa catgttttgg ttgtattttg gattcctagt gtagtttcgg tgatcaatgc   240
cgtctacttt agtgtgttct acttcccttt attttgtttc ttttttactt tttccttaa   300
ctatattgta ggaaaaaaaa aatccttat caagcatttta tcaagaacgg agtttgcttt  360
ttaattttcc cttcataaca ttccatcaga attcagtttt gctttgcttt ctaaattacg   420
ttcaaatcag ggatgataat cggttaggta atatatacag tacccccttgc atagtcacgt   480
ttgaaaaata taatcatact tagttcggta acaatttaaa ttatcattct cgtaatcatt   540
agctacttat gcactcatat ccgtatccgc tacttgctct tgtcgtaagt caataaatta   600
atataaaaaa aatacttaaaa cttgttacaa ctaaattaaa aatttatttt taaatcattc   660
aagcaccagt cagcatcatc acaccaaaag ttaggcccga atagtttgaa attagaaagc   720
tcgcaattga ggtctacagg ccaaattcgc tcttagccgt acaatattac tcaccggatc   780
ctaaccggtg tgatcatggg ccgcgattaa aaatctcaat tatatttggt ctaatttagt   840
ttggtattga gtaaaacaaa ttcgaaccaa ccaaaatat aaatatatag ttttttatata   900
tatgccttta agactttta tagaattttc tttaaaaaat atctagaaat atttgcgact   960
cttctggcat gtaatatttc gttaaatatg aagtgctcca ttttattaa ctttaaataa  1020
ttggttgtac gatcactttc ttatcaagtg ttactaaaat gcgtcaatct ctttgttctt  1080
ccatattcat atgtcaaaac ctatcaaaat tcttatatat ctttttcgaa tttgaagtga  1140
aatttcgata atttaaaatt aaatagaaca tatcattatt taggtatcat attgattttt  1200
atacttaatt actaaatttg gttaactttg aaagtgtaca tcaacgaaaa attagtcaaa  1260
cgactaaaat aaaataaata catgtgttat taagaaaatt ctcctataag aatattttaa  1320
tagatcatat gtttgtaaaa aaaattaatt tttactaaca catatattta cttatcaa    1378
```

| SEQ ID NO: 13 | moltype = DNA length = 23 |
| --- | --- |
| FEATURE | Location/Qualifiers |
| source | 1..23 |
| | mol_type = other DNA |
| | organism = synthetic construct |

SEQUENCE: 13
```
cattgaaata tgttagcaag ttc                                           23
```

| SEQ ID NO: 14 | moltype = DNA length = 25 |
| --- | --- |
| FEATURE | Location/Qualifiers |
| source | 1..25 |
| | mol_type = other DNA |
| | organism = synthetic construct |

SEQUENCE: 14

```
ccaacccggg caccttctcc tctga                                            25

SEQ ID NO: 15           moltype = DNA  length = 25
FEATURE                 Location/Qualifiers
source                  1..25
                        mol_type = other DNA
                        organism = synthetic construct
SEQUENCE: 15
ttgataagta aatatatgtg ttagt                                            25

SEQ ID NO: 16           moltype = DNA  length = 1398
FEATURE                 Location/Qualifiers
source                  1..1398
                        mol_type = other DNA
                        organism = synthetic construct
SEQUENCE: 16
ccaacccggg caccttctcc tctgatttcg ccgccgccat gatcaagatg ggagacatta      60
gtcctctcac tggctccaat ggagaaatca ggaagaattg tagaaggatt aactaatttg     120
attcagtctt gaatattaag ggtcctacac atacgcaagc aatttaattg tgtttaataa     180
gttgttaaaa catgtttttgg ttgtattttg gattcctagt gtagtttcgg tgatcaatgc    240
cgtctacttt agtgtgttct acttcccttt attttttgttt ctttttttact ttttccttaa   300
ctatattgta ggaaaaaaaa aatccttat caagcattta tcaagaacgg agtttgcttt     360
ttaattttcc cttcataaca ttccatcaga attcagtttt gcttttgctt ctaaattacg     420
ttcaaatcag ggatgataat cggttaggta atatatacag taccccttgc atagtcacgt     480
ttgaaaaata taatcatact tagttcgtta caaatttaaa ttatcattct cgtaatcatt     540
agctacttat gcactcatat ccgtatccgc tacttgctct tgtcgtaagt caataaatta     600
atataaaaaa atacttaaaa cttgttacaa ctaaattaaa aatttatttt taaatcattc     660
aagcaccagt ttccattgaa atatgttagc aagttccatc acaccaaaag ttaggcccga     720
atagtttgaa attagaaagc tcgcaattga ggtctacagg ccaaattcgc tcttagccgt     780
acaatattac tcaccggatc ctaaccggtg tgatcatgaa ccgcgattaa aaatctcaat     840
tatatttggt ctaatttagt ttggtattga gtaaaacaaa ttcgaaccaa accaaaatat     900
aaatatatag tttttatata tatgccttta agacttttta tagaatttc tttaaaaat      960
atctagaaat atttgcgact cttctggcat gtaatatttc gttaaatatg aagtgctcca   1020
tttttattaa ctttaaataa ttggttgtac gatcacttttc tatcaagtg ttactaaaat   1080
gcgtcaatct ctttgttctt ccatattcat atgtcaaaac ctatcaaaat tcttatatat   1140
cttttttcgaa tttgaagtga aatttcgata atttaaaatt aaatagaaca tatcattatt  1200
taggtatcat attgattttt atacttaatt actaaatttg gttaactttg aaagtgtaca   1260
tcaacgaaaa attagtcaaa cgactaaaat aaataaatat catgtgttat taagaaaatt   1320
ctcctataag aaatatttaa tagatcatat gttttgtaaaa aaaattaatt tttactaaca   1380
catatattta cttatcaa                                                 1398

SEQ ID NO: 17           moltype = DNA  length = 10232
FEATURE                 Location/Qualifiers
source                  1..10232
                        mol_type = other DNA
                        organism = synthetic construct
SEQUENCE: 17
ctgtcgttgg attcacagaa cattgacgcc agttttcact tcgttatctt tgaattcatt      60
aaaatcgaat ctctcaccta tacccccca tttttctaat ccatcataat caaaattcat     120
aaatgaatca gttaccatta ccataatacc ttttgaaaa tgagtttgaa taatcagtat     180
ctttagaaaa ctaattaaga aattaaataa aaaatattta tcatgaagat gagtgtaaga    240
aaaattatga aaagtataac tttatacatt tctataaaat tatttttct tttaatttct    300
taattaatat cctaagtaaa tgagttaata tttatctttc aaaaattctt atagtcgcca    360
attaattttc ccatgcaatg acaacttgtc cgtattctac gtggtaggtt aggctacctg    420
ccgagacaaa ttgccttgag acaaattcaa tagagaaccc ttccaaggga ccattataaa   480
tagaaacttt tcattaaccg ataagccaca ccctttcaat caaacacaaa cacttgaagt   540
actaagttag tgtgtttgag caaattaact atggcttcgt tttgttctag attgacaatt    600
tgtttggctc tgtttgtcct catatggggg agtgccaatg cacaactttc tacaaacttt    660
tactaccatt catgtccaaa cctcttctcc tctgtgaaat ccacagtgca atctgccata    720
tctaaggaga cccgcatggg tgcttctctc cttcgcttgt tcttccacga ttgctttgtc    780
aatgtaattt atttgcacct tctcccactt acatacaaat atgctaagct tacatatagc    840
tcctctttct accacttgca tgcatcatct aattttgttt gaaacaacac ttgttccttt    900
tattatacac atcatctttg ataaaatttt gtcgtgtgca actttttttt agtgtgttaa    960
tcagttctat gatgatacta ttagttaaga aattttaag cacttaataa accattttaa   1020
gtactttaac cgttcaatga tattatatat ttaaagataa taaatatttc tgcttttgtt   1080
tctatattag tgtagttaag aaccttctta cttcttagct agctaaatat taatgagtaa   1140
acattaacaa atgcagggat gtgatggttc aattctattg gatgacacat caagcttcac   1200
cggagagaag aacgcaaacc ccaacaggaa ctctgctcgt ggattcgagg ttattgacaa   1260
cattaaatca gccgtggaga aagtgtgtcc aggagttgtt tcctgcgcag atatccttgc   1320
catcgctgcc agagactctg ttcagattgt aagtggtcaa acaaccaaca aaacacatt    1380
aaactaaatc attaaattgt acatatcaaa attaattacc aatttagtac cacacatgca   1440
attaaagaga catttttgtt gattttgatc aatatagctt ggaggcccta catgaatgt    1500
taaacttgga agaagagacg ctagaactgc tagccaatct gctgctaaca atggcatccc   1560
tgcacccact tcaaaaccta accaactcat ctcaagattt agcgctcttg gacttttcac   1620
caaggacttg gtcgccttgt ccggtacaaa acatatatca cataatttc caattaatta   1680
catttcaatc atatagtaaa atttctcaat taattaggaa catgagaaac ttatagtcac   1740
acgttctttt gttgaggaat attgcatggt ttaaatttgc tttcattagg tggtcacaca   1800
attgacaag caaggtgcac aaacttcaga gcccgcatct acaacgagac caacatgaa    1860
accgcatttg caaggactag gcagcaaagc tgccctagaa catcagggtc aggggacaac   1920
```

```
aatctggcac cacttgatct tcaaactcca accagctttg acaactacta cttcaagaac  1980
ctcgttcaga agaagggtct cctccactct gatcagcaac tgttcaacgg tgggtccacc  2040
gactccattg tgcgtggcta cagcaccaac ccgggcacct tctcctctga tttcgccgcc  2100
gccatgatca agatgggaga cattagtcct ctcactggct ccaatggaga aatcaggaag  2160
aattgtagaa ggattaacta atttgattca gtcttgaata ttaagggtcc tacacatacg  2220
caagcaattt aattgtgttt aataagttgt taaaacatgt tttggttgta ttttggattc  2280
ctagtgtagt ttcggtgatc aatgccgtct actttagtgt gttctacttc cctttatttt  2340
tgtttctttt ttacttttc cttaactata ttgtaggaaa aaaaaaatcc tttatcaagc  2400
atttatcaag aacggagttt gcttttaat tttcccttca taacattcca tcagaattca  2460
gttttgcttt tgcttctaaa ttacgttcaa atcagggatg ataatcggtt aggtaatata  2520
tacagtaccc cttgcatagt cacgtttgaa aaatataatc atacttagtt cggtaacaat  2580
ttaaattatc attctcgtaa tcattagcta cttatgcact catatccgta tccgctactt  2640
gctcttgtcg taagtcaata aattaatata aaaaaatact taaaacttgt tacaactaaa  2700
ttaaaaattt attttttaaat cattcaagca ccagttttcca ttgaaaatatg ttagcaagtt  2760
ccatcacacc aaaagttagg cccgaatagt ttgaaattag aaagctcgca attgaggtct  2820
acaggccaaa ttcgctctta gccgtacaat attactcacc ggatcctaac cggtgtgatc  2880
atgggccgcg attaaaaatc tcaattatat ttggtctaat ttagttttggt attgagtaaa  2940
acaaattcga accaaaccaa aatataaata tagtttttt atatatatgc ctttaagact  3000
ttttatagaa ttttctttaa aaaatatcta gaaatatttg cgactcttct ggcatgtaat  3060
atttcgttaa atatgaagtg ctccattttt attaacttta aataattggt tgtacgatca  3120
cttctttatc aagtgttact aaaatgcgtc aatctctttt ttcttccata ttcatatgtc  3180
aaaacctatc aaaattctta tatatccttt tcgaatttga agtgaaattt cgataattta  3240
aaattaaata gaacatatca ttatttaggt atcatattga tttttatact taattactaa  3300
atttggttaa ctttgaaagt gtacatcaac gaaaaattag tcaaacgact aaaataaata  3360
aatatcatgt gttattaaga aaattctcct ataagaaatat tttaatagat catatgttttg  3420
taaaaaaaat taatttttac taacacatat atttacttat caaaaatttg acaaagtaag  3480
attaaaataa tattcatcta acaaaaaaaa aaccagaaaa tgctgaaaac ccggcaaaac  3540
cgaaccaatc caaaccgata tagttggttt ggtttgatttt tgatataaac cgaaccaact  3600
cggtccattt gcacccctaa tcataatagc tttaatattt caagatatta ttaagttaac  3660
gttgtcaata tcctggaaat tttgcaaaat gaatcaagcc tatatggctg taatatgaat  3720
ttaaaagcag ctcgatgtgg tggtaatatg taatttactt gattctaaaa aaatatccca  3780
agtattaata atttctgcta ggaagaaggt tagctacgat ttacagcaaa gccagaatac  3840
aatgaaccat aaagtgattg aagctcgaaa tatacgaagg aacaaatatt tttaaaaaaa  3900
tacgcaatga cttggaacaa aagaaagtga tatatttttt gttcttaaac aagcatcccc  3960
tctaaagaat ggcagttttc ctttgcatgt aactattatg ctcccttcgt tacaaaaatt  4020
ttggactact attgggaact tcttctgaaa atagtggcca ccgcttaatt aaggcgcgcc  4080
atgcccgggc aagcggccgc acaagtttgt acaaaaaagc aggctccgcg gtgactgact  4140
gaaaagcttg tcgacctgca ggtcaacgga tcaggatatt cttgtttaag atgttgaact  4200
ctatggaggt ttgtatgaac tgatgatcta ggaccggata agttcccttc ttcatagcga  4260
acttattcaa agaatgtttt gtgtatcatt cttgttacat tgttattaat gaaaaaatat  4320
tattggtcat tggactgaac acgagtgtta aatatggacc aggccccaaa taagatccat  4380
tgatatatga attaaataac aagaataaat cgagtcacca aaccacttgc cttttttaac  4440
gagacttgtt caccaacttg atacaaaagt cattatccta tgcaaatcaa taatcataca  4500
aaaatatcca ataacactaa aaaattaaaa gaaatggata atttcacaat atgttatacg  4560
ataaagaagt tacttttcca agaaattcac tgatttatata agcccacttg cattagataa  4620
atggcaaaaa aaaacaaaaa ggaaagaaa taaagcacga agaattctag aaaatacgaa  4680
atacgcttca atgcagtggg accccacggtt caattattgc caattttcag ctccaccgta  4740
tatttaaaaa ataaaacgat aatgctaaaa aaatataaat cgtaacgatc gttaaatctc  4800
aacggctgga tcttatgacg accgttagaa attgtggttg tcgacgagtc agtaataaac  4860
ggcgtcaaag tggttgcagc cggcacacac gagtcgtgtt tatcaactca aagcacaaat  4920
acttttcctc aacctaaaaa taaggcaatt agccaaaaac aactttgcgt gtaaacaacg  4980
ctcaatacac gtgtcatttt attattagct attgcttcac cgcctttagct ttctcgtgac  5040
ctagtcgtcc tcgtcttttc ttcttcttct tctataaaac aatacccaaa gcttcttctt  5100
cacaattcag atttcaattt ctcaaaatct taaaaacttt ctctcaattc tctctaccgt  5160
gatcaaggta aatttctgtg ttccttattc tctcaaaatc ttcgattttg ttttcgttcg  5220
atcccaattt cgtatatgtt ctttggttta gattctgtta atcttagatc gaagacgatt  5280
ttctgggttt gatcgttaga tatcatctta attctcgatt agggtttcat aaatatcatc  5340
cgatttgttc aaaataatttg agttttgtcg aataattact cttcgatttg tgatttctat  5400
ctagatctgg tgttagtttc tagtttgtgc gatcgaattt gtcgattaat ctgagttttt  5460
ctgattaaca gagatctcca tggctcagac cactctccaa atcacaccca ctggtgccac  5520
cttgggtgcc acagtcactg tgttcaccct tgccacactt gacgatgctg gtttcgctgc  5580
cctccatgca gcctggcttc aacatgcact cttgatcttc cctgggcaac acctcagcaa  5640
tgaccaacag attaccttg ctaaacgctt tggagcaatt gagaggattg gcggaggtga  5700
cattgttgcc atatccaatg tcaaggcaga tggcacagtg cgccagcatt ctcctgcctga  5760
gtgggatgac atgatgaagg tcattgtggg caacatggcc tggcacgccg actcaaccta  5820
catgccagtc atggctcaag gagctgtgtt cagcagcagaa gttgtcccag cagttggggg  5880
cagaacctgc tttgctgaca tgagggcagc ctacgatgcc cttgatgagg caacccgtgc  5940
tcttgttcac caaaggtctg ctcgtcactc ccttgtgtat tctcagagca agtgggaca  6000
tgtccaacag gcccgggtcag cctacatagg ttatggcatg gacaccactg caactcctct  6060
cagaccattg gtcaaggtgc atcctgagac tggaagcccc agcctcttga tcggccgcca  6120
tgcccatgcc atccctggca tggatgcagc tgaatcagag cgcttccttg aaggacttgt  6180
tgactgggcc tgccaggctc ccagagtcca tgctcaccaa tgggctgctg gagatgtggt  6240
tgtgtgggac aaccgctgtt tgctccaccg tgctgagccc tgggatttca gttgccacg  6300
tgtgatgtgg cactccagac tcgctggacg cccagaaact agggtgctg ccttggttg  6360
agtagttagc ttaatcacct agagctcggt caccagcata attttttatta atgtactaaa  6420
ttactgtttt gttaaatgca atttttgcttt tcgggatttt taatatcaaa atctatttag  6480
aaatacacaa tattttgttg caggcttgct ggagaatcga tctgctatca taaaaaattac  6540
aaaaaatttt tatttgcctc aattattttta ggattggtat taaggacgct taaattattt  6600
gtcgggtcac tacgcatcat tgtgattgag aagatcagcg atacgaaata ttcgtagtac  6660
```

```
tatcgataat ttatttgaaa attcataaga aaagcaaacg ttacatgaat tgatgaaaca    6720
atacaaagac agataaagcc acgcacattt aggatattgg ccgagattac tgaatattga    6780
gtaagatcac ggaatttctg acaggagcat gtcttcaatt cagcccaaat ggcagttgaa    6840
atactcaaac cgcccccatat gcaggagcgg atcattcatt gtttgtttgg ttgcctttgc   6900
caacatggga gtccaaggtt gcggccgcgc gccgacccag ctttcttgta caaagtggtt    6960
gcggccgctt aattaaattt aaatgcccgg gcgtttaaac gcggccgctt aattaaggcc    7020
ggcctgcagc aaacccagaa ggtaattatc caagatgtag catcaagaat ccaatgttta    7080
cgggaaaaac tatggaagta ttatgtaagc tcagcaagaa gcagatcaat atgcggcaca    7140
tatgcaacct atgttcaaaa atgaagaatg tacagataca agatcctata ctgccagaat    7200
acgaagaaga atacgtagaa attgaaaaag aagaaccagg cgaagaaaag aatcttgaag    7260
acgtaagcac tgacgacaac aatgaaaaga agaagataag gtcggtgatt gtgaaagaga    7320
catagaggac acatgtaagg tggaaaatgt aagggcggaa agtaacctta tcacaaagga    7380
atcttatccc ccactactta tccttttata tttttccgtg tcattttttgc ccttgagctt    7440
tcctatataa ggaaccaagt tcggcatttg tgaaaacaaa aaaaaatttg gtgtaagcta    7500
ttttctttga agtactgagg atacaacttc agagaaattt gtaagtttgt agatctccat    7560
gtctccggag aggagaccag ttgagattag gccagctaca gcagctgata tggccgcggt    7620
ttgtgatatc gttaaccatt acattgagac gtctacagtg aactttagga cagagccaca    7680
aacaccacaa gagtggattg atgatctaga gaggttgcaa gatagatacc cttggttggt    7740
tgctgaggtt gagggtgttg tggctggtat tgcttacgct gggccctgga aggctaggaa    7800
cgcttacgat tggacagttg agagtactgt ttacgtgtca cataggcatc aaaggttggg    7860
cctaggatcc acattgtaca cacatttgct taagtctatg gaggcgcaag gttttaagtc    7920
tgtggttgct gttataggcc ttccaaacga tccatctgtt aggttgcatg aggcttttgg    7980
atacacagcc cggggtacat tgcgcgcagc tggatacaag catggtggat ggcatgatgt    8040
tggtttttgg caaagggatt ttgagttgcc agctcctcca aggccagtta ggccagttac    8100
ccagatctga ggtaccctga gcttgagctt atgagcttat gagcttagag ctcggatcca    8160
ctagtaacgg ccgccagtgt gctggaattc gcccttgact agataggcgc ccagatccgg    8220
ggcaatagct tcttagcgcc atcccgggtt gatccctatct gtgttgaaat agttgcggtg    8280
ggcaaggctc tcttttcagaa agacaggcgg ccaaaggaac ccaaggtgag gtgggctatg    8340
gctctcagtt ccttgtggaa gcgcttggtc taaggtgcag aggtgttagc gggatgaagc    8400
aaaagtgtcc gattgtaaca agatatgttg atcctacgta agatattaa agtatgtatt    8460
catcactaat ataatcagtg tattccaata tgtactacga tttccaatgt ctttattgtc    8520
gccgtatgta atcggcgtca caaaataatc cccgtgact ttcttttaat ccaggatgaa    8580
ataatatgtt attataattt ttgcgatttg gtccgttata ggaattgaag tgtgcttgcg    8640
gtcgccacca ctcccatttc ataatttttac atgtattttga aaaataaaaa tttatggtat    8700
tcaattttaaa cacgtatact tgtaaagaat gatatcttga aagaaatata gtttaaatat    8760
ttattgataa aataacaagt caggtattat agtccaagca aaaacataaa tttattgatg    8820
caagttaaa ttcagaaata tttcaataac tgattatatc agctggtaca ttgccgtaga    8880
tgaaagactg agtgcgatat tatggtgtaa tacatagcgg ccgggtttct agtcaccggt    8940
taggatccgt ttaaactcga ggctagcgca tgcacataga cacacacatc atctcattga    9000
tgcttggtaa taattgtcat tagattgttt ttatgcatag atgcactcga aatcagccaa    9060
ttttagacaa gtatcaaacg gatgtgactt cagtacatta aaaacgtccg caatgtgtta    9120
ttaagttgtc taagcgtcaa tattttaatt cttaacaatc aatatttttaa ttcttaaact    9180
ttattaaatc taacaataaa ctgtaagaac taattcttaa acttcaataa acaatactgc    9240
gttttagtaa ttaaattaat aatatataga tatagatata taatttgtca acatattctt    9300
acctattttt ccattgaaat atgttagcaa gttcaaaaaa agttttgaca aaaaactcta    9360
ctatctttg tttcatttac tttatgtgag ggatataata gtaatataac atttagttta    9420
tttaaagaaa ataaaaagt taatttctct ttctgccact gatactctat ggtggagaa    9480
tccgatgcag tggtggagcc tggcctcgac acataagtgt gacgacgcag ctgttgaaga    9540
gatctgattc gacggtgggg taatgcatgg tggttgacag gttgatgggt ggagaagacg    9600
taattgctac cgccgtcaac ggaggaagga gcaaagatgt ctcgtatgtg aaaattatgc    9660
ggttggagtc ccgtttcatt ccctttaaaa aaatccctty atggttgcaa tgcaaattaa    9720
aaattgaaaa aataattaat tgttcaaatt aaagatttag catgaaaaaa aaaacactta    9780
attgtgccca tgactccatg acctgcgtaa cttgggaagg aaaggaattt ttttgctaaa    9840
ggaaggcatg ggaagatgag agaggagaga gaatcagtgg aagtgagaga aattaacttt    9900
ttgtttttta aaaactaaat attatattac tattatatat atatatat atatataaa       9960
gatttttttag ctggattctt gatataaaaa atttctcacc atatttatta ttatatattt   10020
ttttggagat ctcaaaaaag gaagttggat ttcctctcaa taactctaaa aaattattcc   10080
tatttcaaaa aatattttt atgtctttct ctaattgatg aataatatct atttaagtat    10140
atttttattgt gaaatccaca aaagtgactg ataaatctaa tttaggatct accattagag   10200
aaaaataaat aaattcttat attatatgtg at                                  10232

SEQ ID NO: 18           moltype = AA   length = 1307
FEATURE                 Location/Qualifiers
source                  1..1307
                        mol_type = protein
                        organism = unidentified
SEQUENCE: 18
MTQFEGFTNL YQVSKTLRFE LIPQGKTLKH IQEQGFIEED KARNDHYKEL KPIIDRIYKT     60
YADQCLQLVQ LDWENLSAAI DSYRKEKTEE TRNALIEEQA TYRNAIHDYF IGRTDNLTDA    120
INKRHAEIYK GLFKAELFNG KVLKQLGTVT TTEHENALLR SFDKFTTYFS GFYENRKNVF    180
SAEDISTAIP HRIVQDNFPK FKENCHIFTR LITAVPSLRE HFENVKKAIG IFVSTSIEEV    240
FSFPFYNQLL TQTQIDLYNQ LLGGISREAG TEKIKGLNEV LNLAIQKNDE TAHIIASLPH    300
RFIPLFKQIL SDRNTLSFIL EEFKSDEEVI QSFCKYKTLL RNENVLETAE ALFNELNSID    360
LTHIFISHKK LETISSALCD HWDTLRNALY ERRISELTGK ITKSAKEKVQ RSLKHEDINL    420
QEIISAAGKE LSEAFKQKTS EILSHAHAAL DQPLPTTLKK QEEKEILKSQ LDSLLGLYHL    480
LDWFAVDESN EVDPEFSARL TGIKLEMEPS LSFYNKARNY ATKKPYSVEK FKLNFQMPTL    540
ASGWDVNKEK NNGAILFVKN GLYYLGIMPK QKGRYKALSF EPTEKTSEGF DKMYYDYFPD    600
AAKMIPKCST QLKAVTAHFQ THTTTPILLSN NFIEPLEITK EIYDLNNPEK EPKKFQTAYA    660
KKTGDQKGYR EALCKWIDFT RDFLSKYTKT TSIDLSSLRP SSQYKDLGEY YAELNPLLYH    720
```

```
ISFQRIAEKE IMDAVETGKL YLFQIYNKDF AKGHHGKPNL HTLYWTGLFS PENLAKTSIK   780
LNGQAELFYR PKSRMKRMAH RLGEKMLNKK LKDQKTPIPD TLYQELYDYV NHRLSHDLSD   840
EARALLPNVI TKEVSHEIIK DRRFTSDKFF FHVPITLNYQ AANSPSKFNQ RVNAYLKEHP   900
ETPIIGIDRG ERNLIYITVI DSTGKILEQR SLNTIQQFDY QKKLDNREKE RVAARQAWSV   960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRN              1307

SEQ ID NO: 19          moltype = DNA   length = 20
FEATURE                Location/Qualifiers
source                 1..20
                       mol_type = other DNA
                       organism = synthetic construct
SEQUENCE: 19
cattcaagca ccagtcagca                                                20

SEQ ID NO: 20          moltype = DNA   length = 2730
FEATURE                Location/Qualifiers
source                 1..2730
                       mol_type = other DNA
                       organism = synthetic construct
SEQUENCE: 20
ctgtcgttgg attcacagaa cattgacgcc agttttcact tcgttatctt tgaattcatt    60
aaaatcgaat ctctcaccta tacccccccca tttttctaat ccatcataat caaaattcat   120
aaatgaatca gttaccatta ccataatacc tttttgaaaa tgagtttgaa taatcagtat   180
ctttagaaaa ctaattaaga aattaaataa aaaatattta tcatgaagat gagtgtaaga   240
aaaattatga aaagtataac tttatacatt tctataaaat tatttttct tttaatttct   300
taattaatat cctaagtaaa tgagttaata tttatctttc aaaaattctt atagtcgcca   360
attaattttc ccatgcaatg acaacttgtc cgtattctac gtggtaggtt aggctacctg   420
ccgagacaaa ttgccttgag acaaattcaa tagagaaccc ttccaaggga ccattataaa   480
tagaagaactt tcattaaccg ataagccaca ccctttcaat caaacacaaa cacttgaagt   540
actaagttag tgtgtttgag caaattaact atggcttcgt tttgttctag attgacaagt   600
tgtttggctc tgtttgtcct catatggggg agtgccaatg cacaactttc tacaaacttt   660
tactaccatt catgtccaaa cctcttctcc tctgtgaaat ccacagtgca atctgccata   720
tctaaggaga cccgcatggg tgcttctctc cttcgcttgt tcttccacga ttgctttgtc   780
aatgtaattt atttgcacct tctcccactt acatacaaat tacataagct tacatatagc   840
tcctcttttct accacttgca tgcatcatct aattttgttt gaaacaacac ttgttccttt   900
tattatacac atcatctttg ataaaatttt gtcgtgtgca acttttttt agtgtgttaa   960
tcagttctat gatgatacta ttagttaaga aattttaatg cacttaataa accattttaa  1020
gtacttttaac cgttcaatga tattatatat ttaaagataa taaatatttc tgcttttgtt  1080
tctatattag tgtagttaag aaccttctta cttcttagct agctaaatat taatgagtaa  1140
acattaacaa atgcagggat gtgatggttc aattctattg gatgacacat caagcttcac  1200
cggagagaag aacgcaaacc ccaacaggaa ctctgctcgt ggattcgagg ttattgacaa  1260
cattaaatca gccgtggaga aagtgtgtcc aggagttgtt tcctgcgcag atatcccttg  1320
catcgctgcc agagactctg ttcagattgt aagtggtcaa acaaccaaca aaaacacatt  1380
aaaactaaatc attaaattgt acatatcaaa attaattacc aatttagtac cacacatgca  1440
attaaagaga acattttgtt gattttgatc aatatagctt ggaggccta catggaatgt  1500
taaacttgga agaagagacg ctagaactgc tagccaatgc gctgctaaca atggcatccn  1560
tgcaccccact tcaaaccttta accaactcat ctcaagattt agcgctcttg gactttccac  1620
caaggacttg gtcgccttgt ccggtacaaa acatatatca cataattttc caattaatta  1680
catttcaatc atatagtaaa atttctcaat taattaggaa catgagaaac ttatagtcac  1740
acgttctttt gttgaggaat attgcatggt ttaattttgc tttcattagg tggtcacaca  1800
attggacaag caaggtgcac aaacttcaga gcccgcatct acaacgagac caacatagaa  1860
accgcatttg caaggactag gcagcaaagc tgccctagaa catcagggtc aggggacaac  1920
aatctggcac cacttgatct tcaaactcca accagctttg acaactacta cttcaagaac  1980
ctcgttcaga agaagggtct cctccactct gatcagcaac tgttcaacgg tgggtccaca  2040
gactccattg tgcgtggcta cagcaccaac ccgggcacct tctcctctga tttcgccgcc  2100
gccatgatca agatgggaga cattagtcct ctcactggct ccaatggaga aatcaggaag  2160
aattgtagaa ggattaacta atttgattca gtcttgaata ttaagggtcc tacacatacg  2220
caagcaattt aattgtgttt aataagttgt taaaacatgt tttggttgta ttttggattc  2280
ctagtgtagt ttcggtgatc aatgccgtct acttttagtg gttctacttc cctttattt  2340
tgtttctttt ttactttttc cttaactata ttgtaggaaa aaaaaaatcc tttatcaagc  2400
atttatcaag aacggagttt gctttttaat tttcccttca taacattcca tcagaattca  2460
gttttgcttt tgcttctaaa ttacgttcaa atcaggatg ataatcggtt aggtaatata  2520
tacagtaccc cttgcatagt cacgtttgaa aaatataatc atacttagtt cggtaacaat  2580
ttaaattatc attctcgtaa tcattagcta cttatgcact catatccgta tccgctactt  2640
gctcttgtcg taagtcaata aattaatata aaaaaatact taaaacttgt tacaactaaa  2700
ttaaaaattt atttttaaat cattcaagca                                   2730

SEQ ID NO: 21          moltype = DNA   length = 20
FEATURE                Location/Qualifiers
source                 1..20
                       mol_type = other DNA
                       organism = synthetic construct
SEQUENCE: 21
aagcgtcaat attttaattc                                                20
```

```
SEQ ID NO: 22           moltype = DNA  length = 1091
FEATURE                 Location/Qualifiers
source                  1..1091
                        mol_type = other DNA
                        organism = synthetic construct
SEQUENCE: 22
attttaattc ttaacaatca atattttaat tcttaaactt tattaaatct aacaataaac    60
tgtaagaact aattcttaaa cttcaataaa caatactgcg ttttagtaat taaattaata   120
atatatagat atagatatat aatttgtcaa catattctta cctattttc cattgaaata    180
tgttagcaag ttcaaaaaaa gttttgacaa aaaactctac tatcttttgt ttcatttact   240
ttatgtgagg gatataatag taatataaca tttagtttat ttaaagaaaa taaaaaagtt   300
aatttctctt tctgccactg atactctatg gtggagagat ccgatgcagt ggtggagcct   360
ggcctcgaca cataagtgtg acgacgcagc tgttgaagag atctgattcg acggtggggt   420
aatgcatggt ggttgacagg ttgatgggtg gagaagacgt aattgctacc gccgtcaacg   480
gaggaaggag caaagatgtc tcgtatgtga aaattatgcg gttgagatgc cgtttcattc   540
cctttaaaaa aatcccttga tggttgcaat gcaaattaaa aattgaaaaa ataattaatt   600
gttcaaatta aagatttagc atgaaaaaaa aaacacttaa ttgtgcccat gactccatga   660
cctgcgtaac ttgggaagga aaggaattt tttgctaaag gaaggcatgg gaagatgaga   720
gaggagagag aatcagtgga agtgagagaa attaactttt tgtttttaa aaactaaata   780
ttatattact attatatata tatatatata tatataaaag atttttagc tggattcttg    840
atataaaaaa tttctcacca tatttattat tatatattt tttggagatc tcaaaaaagg   900
aagttggatt tcttctcaat aactctaaaa aattattcct atttcaaaaa atatttttta   960
tgtctttctc taattgatga ataatatcta tttaagtata ttttattgtg aaatccacaa  1020
aagtgactga taaatctaat ttaggatcta ccattagaaa aaaataaata aattcttata  1080
ttatatgtga t                                                      1091

SEQ ID NO: 23           moltype = DNA  length = 1127
FEATURE                 Location/Qualifiers
source                  1..1127
                        mol_type = other DNA
                        organism = synthetic construct
SEQUENCE: 23
gattcagtct tgaatattaa gggtcctaca catacgcaag caatttaatt gtgtttaata    60
agttgttaaa acatgttttg gttgtatttt ggattcctag tgtagtttcg gtgatcaatg   120
ccgtctactt tagtgtgttc tacttccctt tattttgtt tcttttttac tttttcctta    180
actatattgt aggaaaaaaa aaatcccttta tcaagcattt atcaagaacg gagtttgctt   240
tttaattttc ccttcataac attccatcag aattcagttt tgcttttgct tctaaattac   300
gttcaaatca gggatgataa tcggttaggt aatatataca gtacccctg catagtcacg   360
tttgaaaaat ataatcatac ttagttcggt aacaatttaa attatcattc tcgtaatcat   420
tagctactta tgcactcata tccgtatccg ctacttgctc ttgtcgtaag tcaataaatt   480
aatataaaaa aatacttaaa acttgttaca actaaattaa aaatttattt ttaaatcatt   540
caagtttcca ttgaaatatg ttagcaagtt ccagcatcat cacaccaaaa gttaggcccg   600
aatagtttga aattagaaag ctcgcaattg aggtctacag gccaaattcg ctcttagccg    660
tacaatatta ctcaccggat cctaaccggt gtgatcatgg gccgcgatta aaaatctcaa   720
ttatatttgg tctaatttag tttggtattg agtaaaacaa attcgaacca aaccaaaata   780
taaatatata gttttttatat atatgccttt aagactttt atagaatttt cttttaaaaaa  840
tatctagaaa tatttgcgac tcttctggca tgtaatattt cgttaaatat gaagtgctcc   900
atttttatta acttttaaata attggttgta cgatcacttt cttatcaagt gttactaaaa   960
tgcgtcaatc tctttgttct tccatattca tatgtcaaaa cctatcaaaa ttcttatata  1020
tcttttcga atttgaagtg aaatttcgat aatttaaaat taaatagaac atatcattat   1080
ttaggtatca tattgatttt tatacttaat tactaaattt ggttaac                1127
```

MODIFIED EXCISABLE DAS68416-4 SOYBEAN TRANSGENIC HERBICIDE RESISTANCE LOCUS

CROSS-REFERENCE TO RELATED APPLICATIONS

This is a continuation application of International Application No. PCT/US2021/043,945, filed on Jul. 30, 2021, which claims the benefit of priority to U.S. Provisional Patent Application No. 63/203,137, filed on Jul. 9, 2021, U.S. Provisional Patent Application No. 63/202,569, filed on Jun. 16, 2021, U.S. Provisional Patent Application Nos. 63/201,030 and 63/201,029, filed on Apr. 9, 2021, U.S. Provisional Patent Application Nos. 63/199,951 and 63/199,949, filed on Feb. 4, 2021, U.S. Provisional Patent Application No. 63/199,930, filed on Feb. 3, 2021, and U.S. Provisional Patent Application Nos. 63/059,813, 63/059,860, 63/059,916, and 63/059,963, filed on Jul. 31, 2020, each of which are incorporated herein by reference in their entireties.

REFERENCE TO SEQUENCE LISTING SUBMITTED ELECTRONICALLY

The instant application contains a Sequence Listing which has been submitted electronically in XML formatted and is herein incorporated by reference in its entirety. Said XML copy, created on Nov. 18, 2022, is named "P13650US00_SequenceListing.xml" and is 72,364 bytes in size.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic soybean event which confers resistance to herbicides is the DAS68416-4 transgenic soybean event disclosed in U.S. Pat. No. 9,738,904. DAS68416-4 transgenic soybean plants express an aryloxyalkanoate dioxygenase-12 (AAD-12) protein which confers tolerance to phenoxyacetic acid and pyridyloxyacetic acid herbicides. DAS68416-4 transgenic soybean plants also express a phosphinothricin acetyltransferase (PAT) protein which confers tolerance to the glufosinate herbicide.

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, Proc. Natl Acad. Sci. USA 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic soybean plant cells comprising an INHT27 transgenic locus comprising an originator guide RNA recognition site (OgRRS) in a first DNA junction polynucleotide of a DAS68416-4 transgenic locus and a cognate guide RNA recognition site (CgRRS) in a second DNA junction polynucleotide of the DAS68416-4 transgenic locus are provided. Transgenic soybean plant cells comprising an INHT27 transgenic locus comprising an insertion and/or substitution in a DNA junction polynucleotide of a DAS68416-4 transgenic locus of DNA comprising a cognate guide RNA recognition site (CgRRS) are provided. In certain embodiments, the DAS68416-4 transgenic locus is set forth in SEQ ID NO:1, is present in seed deposited at the ATCC under accession No. PTA-10442 is present in progeny thereof, is present in allelic variants thereof, or is present in other variants thereof. INHT27 transgenic soybean plant cells, transgenic soybean plant seeds, and transgenic soybean plants all comprising a transgenic locus set forth in SEQ ID NO: 2, 3, 17, and allelic variants thereof are provided. Transgenic soybean plant parts including seeds and transgenic soybean plants comprising the soybean plant cells are also provided.

Methods for obtaining a bulked population of inbred seed comprising selfing the aforementioned transgenic soybean plants and harvesting seed comprising the INHT27 transgenic locus from the selfed soybean plant are also provided.

Methods of obtaining hybrid soybean seed comprising crossing the aforementioned transgenic soybean plants to a second soybean plant which is genetically distinct from the first soybean plant and harvesting seed comprising the INHT27 transgenic locus from the cross are provided. Methods for obtaining a bulked population of seed comprising selfing a transgenic soybean plant of comprising SEQ ID NO: 2, 3, 17, and allelic variants thereof and harvesting transgenic seed comprising the transgenic locus set forth in SEQ ID NO: 2, 3, 17, and allelic variants thereof are provided.

A DNA molecule comprising SEQ ID NO: 2, 3, 8, 9, 10, 11, 17, 23, or an allelic variant thereof is provided. Processed transgenic soybean plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a soybean plant cell comprising an INHT27 transgenic locus, comprising the step of detecting a DNA molecule comprising SEQ ID NO: 2, 3, 8, 9, 10, 11, 17, 23, or an allelic variant thereof are provided.

Methods of excising the INHT27 transgenic locus from the genome of the aforementioned soybean plant cells comprising the steps of (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INHT27 transgenic locus flanked by the OgRRS and the CgRRS has been excised.

BRIEF DESCRIPTION OF THE DRAWINGS/FIGURES

FIG. 1 shows a schematic diagram of the DAS68416-4 transgenic locus.

Figure 2:
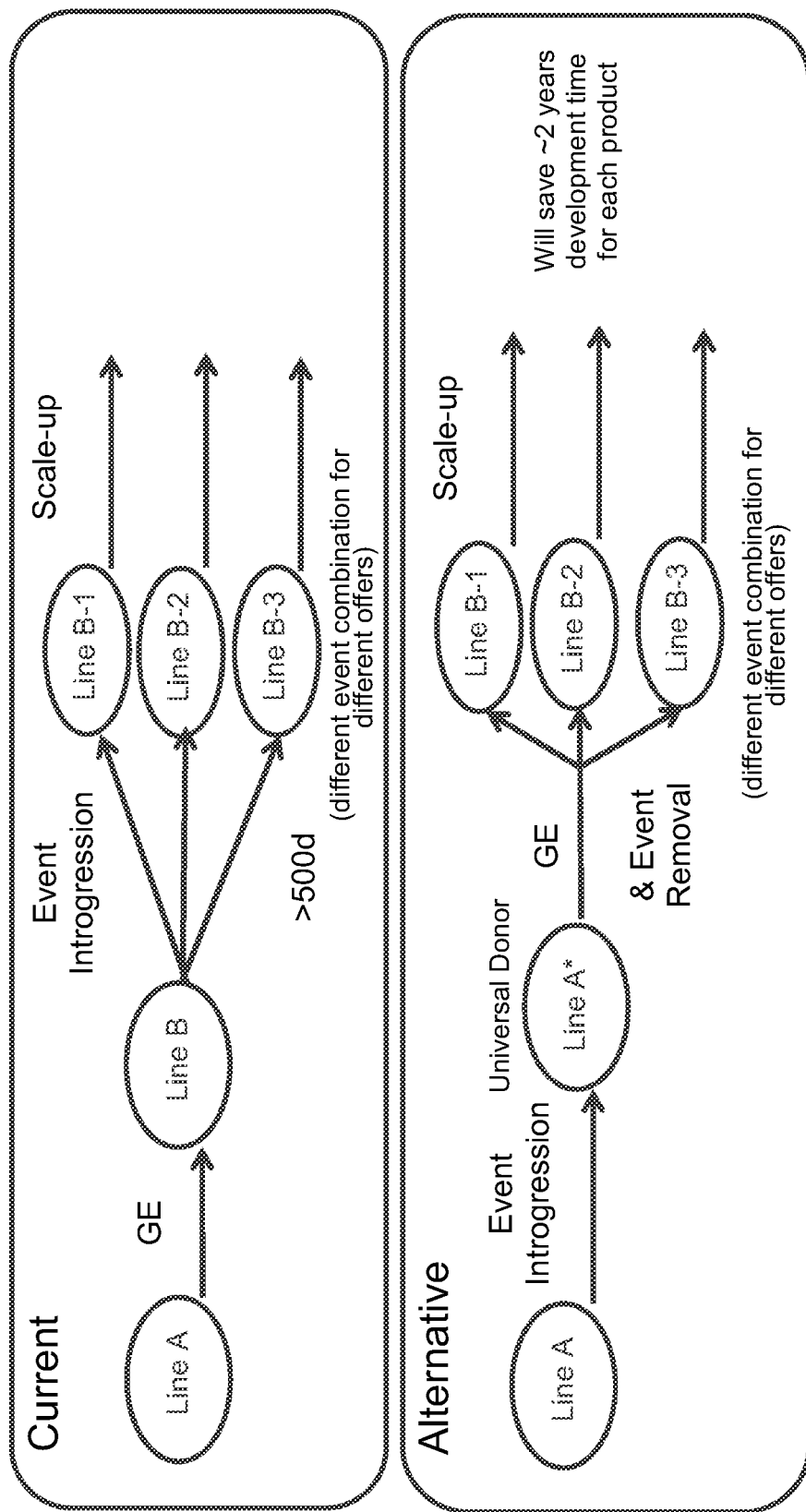

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 3, "GE" refers to genome editing (e.g., including introduction of targeted genetic changes with genome editing molecules) and "Event Removal" refers to excision of a transgenic locus (i.e., an "Event") with genome editing molecules.

Figure 3A:
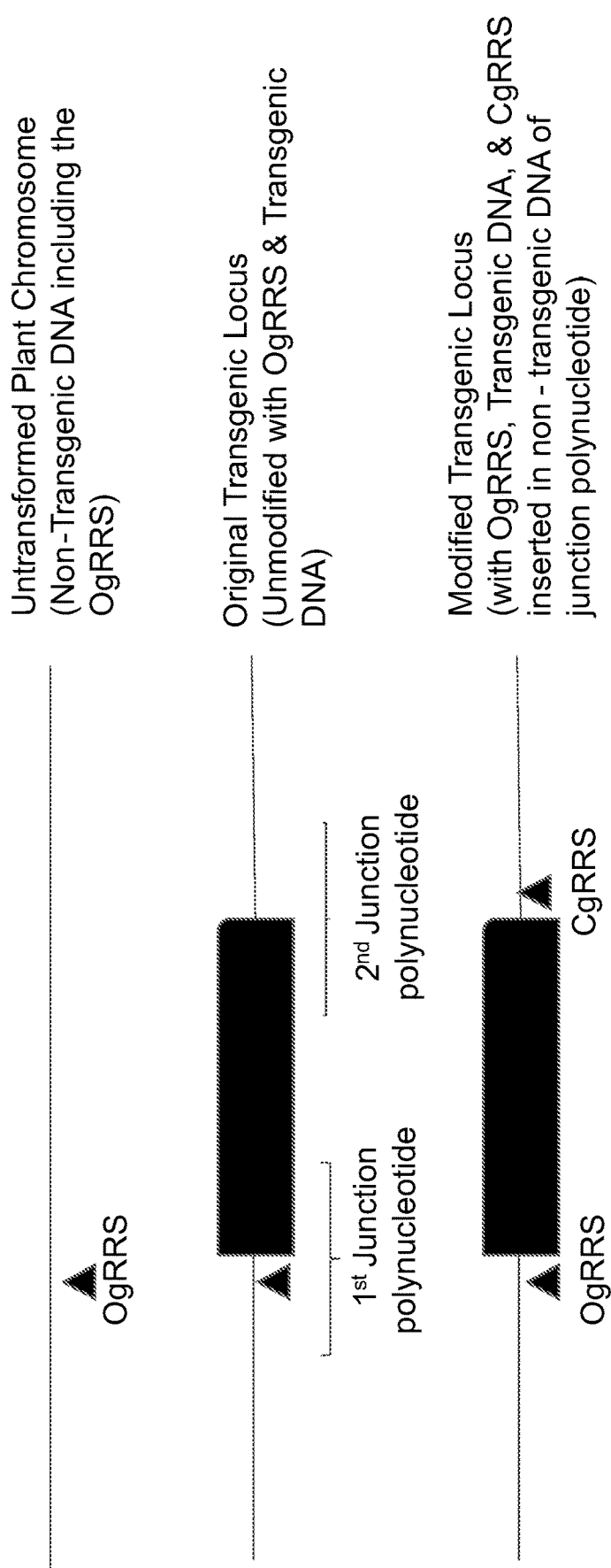

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the 1$^{st}$ junction polynucleotide (middle); and (iii) the modified transgenic locus with a cognate guide RNA inserted into the non-transgenic DNA of the 2$^{nd}$ junction polynucleotide (bottom). FIG. 3B shows a schematic diagram of a non-limiting example of a process where a modified transgenic locus with a cognate guide RNA inserted into the non-transgenic DNA of the 2$^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the 2$^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 3C, cleavage of the modified transgenic locus in the presence of the donor DNA template which has homology to non-transgenic DNA but lacks the OgRRS in the 1$^{st}$ and 2$^{nd}$ junction polynucleotides followed by homology-directed repair processes to provide a plant chromosome where the transgenic locus is excised and non-transgenic DNA present in the untransformed plant chromosome is at least partially restored.

DETAILED DESCRIPTION

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 18.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "DAS68416-4" is used to refer to any of a transgenic soybean locus, transgenic soybean plants and parts thereof including seed set forth in U.S. Pat. No. 9,738,904, which is incorporated herein by reference in its entirety. Representative DAS68416-4 transgenic soybean seed have been deposited with American Type Culture Collection (ATCC, Manassas, Va. 20110-2209 USA) under Accession No. PTA-10442. DAS68416-4 transgenic loci include loci having the sequence of SEQ ID NO:1, the sequence of the DAS68416-4 locus in the deposited seed of Accession No. PTA-10442 and any progeny thereof, as well as allelic variants and other variants of SEQ ID NO:1.

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INHT27" is used to refer either individually collectively to items that include any or all of the DAS68416-4 transgenic soybean loci which have been modified as disclosed herein, modified DAS68416-4 transgenic soybean plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site (i.e., protospacer sequence). In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site (i.e., protospacer sequence), where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in non-transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Various sequences set forth in the sequence listing are described in the following table.

TABLE 1

Description of sequences.

| SEQ ID NO | Description |
| --- | --- |
| 1 | DAS68416-4 transgenic locus. The 5' flank region comprises nucleotides 1-2730 of SEQ ID NO: 1. The transgenic insert extends from nucleotides 2731-9121 of SEQ ID NO: 1. The 3' flanking DNA comprises nucleotides 9122-10212 of SEQ ID NO: 1. |
| 2 | INHT27-1 (G1 Cut) |
| 3 | INHT27-2 (Insertion of 27Bp CgRRS of SEQ ID NO: 9 in 5' junction polynucleotide with gRNA-2 Cut and SEQ ID NO: 23 donor template containing the SEQ ID NO: 9 CgRRS) |
| 4 | gRNA-1 |
| 5 | gRNA-2 |
| 6 | gRNA-3 |
| 7 | OgRRS |
| 8 | CgRRS+ flank DNA (G1 Insert) |
| 9 | CgRRS+ Flank DNA (G2 Insert) |
| 10 | CgRRS+ Flank DNA (G3 Insert) |
| 11 | DAS68416 donor template sequence containing the SEQ ID NO: 8 CgRRS |
| 12 | DAS68416 5' target insertion site |
| 13 | DAS68416-gRNA coding sequence |
| 14 | DAS68416 5' primer |
| 15 | DAS68416 3' primer |
| 16 | DAS68416 CgRRS and flank |
| 17 | INHT27-3 (Insertion of 27 bp CgRRS of SEQ ID NO: 8 with gRNA-1 Cut and SEQ ID NO: 11 donor DNA template containing the SEQ ID NO: 8 CgRRS) |
| 18 | (Cas 12a Nuclease ) (>sp\|U2UMQ6\|CS12A_ACISB CRISPR-associated endonuclease Cas12a OS=Acidaminococcus sp. (strain BV3L6) OX = 1111120 GN = cas12a PE = 1 SV = 1) |
| 19 | DAS68416 5' Junction Polynucleotide |
| 20 | DAS68416 5' plant genomic flanking |
| 21 | DAS68416 3' Junction Polynucleotide |
| 22 | DAS68416 3' plant genomic flanking |
| 23 | INHT27-2 Donor Template for SEQ ID NO: 3 (SEQ ID NO: 9 CgRRS) |

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as soybean and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INHT27 transgenic loci provided here are characterized by polynucleotide sequences that can facilitate as necessary the removal of the INHT27 transgenic loci from the genome. Useful applications of such INHT27 transgenic loci and related methods of making include targeted excision of a INHT27 transgenic locus or portion thereof in certain breeding lines to facilitate recovery of germplasm with subsets of transgenic traits tailored for specific geographic locations and/or grower preferences. Other useful applications of such INHT27 transgenic loci and related methods of making include removal of transgenic traits from certain breeding lines when it is desirable to replace the trait in the breeding line without disrupting other transgenic loci and/or non-transgenic loci. In certain embodiments, soybean genomes containing INHT27 transgenic loci or portions thereof which can be selectively excised with one or more gRNA molecules and RdDe (RNA dependent DNA endonucleases) which form gRNA/target DNA complexes. Such selectively excisable INHT27 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. An example of OgRRS polynucleotide sequences in or near a 3' junction polynucleotide in an DAS68416-4 transgenic locus include SEQ ID NO: 7. OgRRS polynucleotide sequences located in a first junction polynucleotide can be introduced into the second junction polynucleotide using donor DNA templates as illustrated in FIG. 3A as elsewhere described herein. A donor DNA template for introducing the SEQ ID NO: 7 OgRRS into the 5' junction polynucleotide of an DAS68416-4 locus includes the donor DNA template comprising SEQ ID NO: 11 or 23. Double stranded breaks in a 5' junction polynucleotide of SEQ ID NO: 1 can be introduced with the Guide-1, -2, or -3 5 gRNAs, which are respectively encoded by SEQ ID NO: 4, 5, or 6, and a Cas12a nuclease. Integration of the SEQ ID NO: 11, 23, or other donor DNA template comprising the CgRRS into the 5' junction polynucleotide of an DAS68416-4 locus at the double stranded breaks introduced by the gRNAs encoded by SEQ ID NO: 4, 5, or 6 and a Cas12a nuclease can provide an INHT27 locus comprising the CgRRS sequence set forth in SEQ ID NO: 8, 9, or 10. A subsequence comprising a CgRRS which is located in the 5' junction polynucleotide of the INHT27 transgenic locus is set forth in SEQ ID NO: 18. Double stranded breaks in a 5' junction polynucleotide of SEQ ID NO: 1 can be introduced with gRNAs encoded by SEQ ID NO: 4, 5, or 6 and a Cas12a nuclease. A donor DNA template of SEQ ID NO: 11 or the equivalent thereof having longer or shorter homology arms can be used to obtain the CgRRS insertion in the 5' junction polynucleotide that is set forth in SEQ ID NO: 8. An INHT27 transgenic locus containing this CgRRS insertion is set forth in SEQ ID NO: 17. A donor DNA template of SEQ ID NO: 23 or the equivalent thereof having longer or shorter homology arms can be used to obtain the CgRRS insertion in the 5' junction polynucleotide that is set forth in SEQ ID NO: 9. An INIR19 transgenic locus containing this CgRRS insertion of SEQ ID NO: 9 is set forth in SEQ ID NO: 3.

Also provided herein are allelic variants of any of the INHT27 transgenic loci or DNA molecules provided herein. In certain embodiments, such allelic variants of INHT27 transgenic loci include sequences having at least 85%, 90%, 95%, 98%, or 99% sequence identity across the entire length or at least 20, 40, 100, 500, 1,000, 2,000, 4,000, 6,000, 8,000, 9,000, 10,000, or 10,212 nucleotides of SEQ ID NO: 2, 3, or 17. In certain embodiments, such allelic variants of INHT27 DNA molecules include sequences having at least 85%, 90%, 95%, 98%, or 99% sequence identity across the entire length of SEQ ID NO: 2, 3, 8, 9, 10, 11, 16, 17, or 23.

Also provided are unique transgenic locus excision sites created by excision of INHT27 transgenic loci or selectively excisable INHT27 transgenic loci, DNA molecules comprising the INHT27 transgenic loci or unique fragments thereof (i.e., fragments of an INHT27 locus which are not found in an DAS68416-4 transgenic locus), INHT27 plants comprising the same, biological samples containing the DNA, nucleic acid markers adapted for detecting the DNA molecules, and related methods of identifying soybean plants comprising unique INHT27 transgenic locus excision sites and unique fragments of a INHT27 transgenic locus. An example of such an excision site would include an excision site created by excising an INHT27 transgenic locus comprising a CgRRS of SEQ ID NO: 8, 9, or 10 located in a 5' junction polynucleotide with a guide RNA encoded by SEQ ID NO: 13 and a suitable Cas RdDe (e.g., a Cas12a nuclease of SEQ ID NO: 18). DNA molecules comprising unique fragments of an INHT27 transgenic locus are diagnostic for the presence of an INHT27 transgenic locus or fragments thereof in a soybean plant, soybean cell, soybean seed, products obtained therefrom (e.g., seed meal or stover), and biological samples. DNA molecules comprising unique fragments of an INHT27 transgenic locus include DNA molecules comprising the CgRRS include SEQ ID NO: 8, 9, 10, 11, 16, 23, and allelic variants therof.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the soybean DAS68416-4 transgenic locus. The soybean DAS68416-4 transgenic locus is depicted in FIG. 1. Soybean plants comprising the DAS68416-4 transgenic locus and seed thereof have been cultivated, been placed in commerce, and have been described in a variety of publications by various governmental bodies. Databases which have compiled descriptions of the DAS68416-4 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the DAS68416-4 transgenic locus which can be improved by the methods provided herein are set forth or otherwise provided in SEQ ID NO: 1, U.S. Pat. No. 9,738,904, the sequence of the DAS68416-4 locus in the deposited seed of ATCC accession No. PTA-10442, and elsewhere in this disclosure. In certain embodiments provided herein, the DAS68416-4 transgenic locus set forth in SEQ ID NO: 1 or present in the deposited seed of ATCC accession No. PTA-10442 is referred to as an "original DAS68416-4 transgenic locus." Allelic or other variants of the sequence set forth SEQ ID NO: 1, the patent references set forth therein and incorporated herein by reference in their entireties, and elsewhere in this disclosure which may be present in certain variant DAS68416-4 transgenic plant loci (e.g., progeny of deposited seed of accession No. PTA-10442 which contain allelic variants of SEQ ID NO:1 or progeny originating from transgenic plant cells comprising the original DAS68416-4 transgenic locus set forth in U.S. Pat. No. 9,738,904) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, 11,000, 12,000, 13,000 or 13,659 nucleotides of SEQ ID NO: 1. Also provided are plants, plant parts including seeds, genomic DNA, and/or DNA obtained from INHT27 plants which comprise one or more modifications (e.g., via insertion of a CgRRS in a junction polynucleotide sequence) which provide for selective excision of the INHT27 transgenic locus or a portion thereof. Also provided herein are methods of detecting plants, genomic DNA, and/or DNA obtained from plants comprising a INHT27 transgenic locus which contains one or more of a CgRRS, deletions of selectable marker genes, deletions of non-essential DNA, and/or a transgenic locus excision site. A first junction polynucleotide of a DAS68416-4 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INHT27 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the DAS68416-4 transgenic locus of SEQ ID NO: 1, allelic variants thereof, or other variants thereof to obtain an INHT27 transgenic locus. In other embodiments, the OgRRS is found in non-transgenic DNA or transgenic DNA of the 3' junction polynucleotide of the DAS68416-4 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INHT27 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INHT27 transgenic locus, in transgenic DNA of a DNA junction polynucleotide of an INHT27 transgenic locus or can span the junction of the transgenic and non-transgenic DNA of a DNA junction polynucleotide of an INHT27 transgenic locus. An OgRRS can likewise be located in non-transgenic plant genomic DNA of a DNA junction polynucleotide of an INHT27 transgenic locus, in transgenic DNA of a DNA junction polynucleotide of an INHT27 transgenic locus, or can span the junction of the transgenic and non-transgenic DNA of a DNA junction polynucleotide of an INHT27 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INHT27 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 2) comprising two or more of the modified transgenic loci. This elite germplasm containing the modified transgenic loci (e.g., "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed soybean plants comprising the INHT27 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran insects), or a different mode-of-action for the same trait (e.g., resistance to lepidopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INHT27 transgenic locus comprising an OgRRS in non-transgenic DNA of a $1^{st}$ junction polynucleotide sequence and a CgRRS in a $2^{nd}$ junction polynucleotide sequence is deleted with a gRNA and RdDe that recognize the OgRRS and the CgRRS to produce an INHT27 transgenic locus excision site. For example, an INHT27 transgenic locus set forth in SEQ ID NO: 3 or 17 can be deleted with a Cas12a RdDe (e.g. the Cas12a of SEQ ID NO: 18) and a gRNA comprising an RNA encoded by SEQ ID NO: 13. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INHT27 transgenic loci excision sites are provided herein.

In other embodiments, a segment comprising a INHT27 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS (e.g., for INHT27 loci comprising SEQ ID NO: 8, 9, or 10 CgRRS elements in a 5' junction polynucleotide, the Cas12a RdDe of SEQ ID NO: 18 and a gRNA comprising an RNA encoded by SEQ ID NO: 13) and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a DAS68416-4 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe and a single suitable guide RNA directed to the CgRRS and the originator gRNA Recognition Site (OgRRS) to provide for cleavage within the junction polynucleotides which flank an INHT27 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the soybean plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS is created in a DNA sequence are illustrated in Example 2 and FIG. 3.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS (e.g., the Cas12a RdDe of SEQ ID NO: 18 and a gRNA comprising an RNA encoded by SEQ ID NO: 13). A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can lack one or more selectable markers found in an original event (transgenic locus). Original DAS68416-4 transgenic loci (events), including those set forth in SEQ ID NO: 1), U.S. Pat. No. 9,738,904, the sequence of the DAS68416-4 locus in the deposited seed of accession No. PTA-10442 and progeny thereof, contain a selectable marker gene encoding a phosphinotricin acetyl transferase (PAT) protein which confers tolerance to the herbicide glufosinate. In certain embodiments provided herein, the DNA element comprising, consisting essentially of, or consisting of the PAT selectable marker gene of an DAS68416-4 transgenic locus is absent from an INHT27 transgenic locus. The PAT selectable marker cassette can be excised from an original DAS68416-4 transgenic locus by contacting the transgenic locus with one or more gene editing molecules which introduce double stranded breaks in the transgenic locus at the 5' and 3' end of the expression cassette comprising the PAT selectable marker transgene (e.g., an RdDe and guide RNAs directed to PAM sites located at the 5' and 3' end of the expression cassette comprising the PAT selectable marker transgene) and selecting for plant cells, plant parts, or plants wherein the selectable marker has been excised. In certain embodiments, the selectable or scoreable marker transgene can be inactivated. Inactivation can be achieved by modifications including insertion, deletion, and/or substitution of one or more nucleotides in a promoter element, 5' or 3' untranslated region (UTRs), intron, coding region, and/or 3' terminator and/or polyadenylation site of the selectable marker transgene. Such modifications can inactivate the selectable marker transgene by eliminating or reducing promoter activity, introducing a missense mutation, and/or introducing a pre-mature stop codon. In certain embodiments, the selectable PAT marker transgene can be replaced by an introduced transgene. In certain embodiments, an original transgenic locus that was contacted with gene editing molecules which introduce double stranded breaks in the transgenic locus at the 5' and 3' end of the expression cassette comprising the PAT selectable marker transgene can also be contacted with a suitable donor DNA template comprising an expression cassette flanked by DNA homologous to remaining DNA in the transgenic locus located 5' and 3' to the selectable marker excision site. In certain embodiments, a coding region of the PAT selectable marker transgene can be replaced with another coding region such that the replacement coding region is operably linked to the promoter and 3' terminator or polyadenylation site of the PAT selectable marker transgene.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 6,040,497, 8,759,618, 7,157,281, 6,852,915, 7,705,216, 10,316,330, 8,618,358, 8,450,561, 8,212,113, 9,428,765, 9,540,655, 7,897,748, 8,273,959, 8,093,453, 8,901,378, 9,994,863, 7,928,296, and 8,466,346, each of which are incorporated herein by reference in their entireties.

In certain embodiments, INHT27 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (l) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target soybean genes that can be subjected to targeted gene edits to confer useful traits include: (a) ZmIPK1 (herbicide tolerant and phytate reduced soybean; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8

(drought stress tolerance; Shi et al., Plant Biotechnol J. 2017; 15:207-16). Non-limiting examples of target genes in crop plants including soybean which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) used to form an RNA-guided endonuclease/guide RNA complex can specifically bind via hybridization to gRNA hybridization site sequences (i.e., protospacer sequences) in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins (e.g., the Cas12a protein of SEQ ID NO: 18). In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarity to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) Science, 339:819-823; Xing et al. (2014) BMC Plant Biol., 14:327-340. Chemically modified sgRNAs have been demonstrated to be effective in genome editing; see, for example, Hendel et al. (2015) Nature Biotechnol., 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) Nature, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., Sci Adv. 2017 August; 3(8):eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) Nature 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8, 12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e.g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 11, 23, and equivalents thereof with longer or shorter homology arms. In certain embodiments, a donor DNA template can comprise an adapter molecule (e.g., a donor DNA template formed by annealing single stranded DNAs which do not overlap at their 5' and 3' terminal ends) with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an E. coli SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e.g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide. An example of a useful DNA donor template provided herein is a DNA molecule comprising SEQ ID NO: 11, 23, or an equivalent thereof.

Various treatments are useful in delivery of gene editing molecules and/or other molecules to a DAS68416-4 or INHT27 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature*, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a DAS68416-4 or INHT27 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from soybean, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a soybean chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the DAS68416-4 or INHT27 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www [dot]openwetware[dot]org/images/d/d3/Haploid_Arabidopsis_protocol[dot]pdf; (Ravi et al. (2014) *Nature Communications*, 5:5334, doi: 10.1038/ncomms6334). Haploids can also be obtained in a wide variety of monocot plants (e.g., soybean, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing soybean lines that can be used to obtain haploid soybean plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the DAS68416-4 or INHT27 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the DAS68416-4 or INHT27 plant cells in used in the methods provided herein can include dividing cells. Dividing cells can include those cells found in various plant tissues including leaves, meristems, and embryos. These tissues include dividing cells from young soybean leaf, meristems and scutellar tissue from about 8 or 10 to about 12 or 14 days after pollination (DAP) embryos. The isolation of soybean embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a soybean plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INHT27 plant from a INHT27 plant cell that had been subjected to the gene editing or from a regenerable plant structure obtained from that INHT27 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INHT27 plant or its seeds, including: (a) soybean seed meal (defatted or non-defatted); (b) extracted proteins, oils, sugars, and starches; (c) fermentation products; (d) animal feed or human food products (e.g., feed and food comprising soybean seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

EMBODIMENTS

Various embodiments of the plants, genomes, methods, biological samples, and other compositions described herein are set forth in the following sets of numbered embodiments.

1a. A transgenic soybean plant cell comprising an INHT27 transgenic locus comprising an originator guide RNA recognition site (OgRRS) in a first DNA junction polynucleotide of a DAS68416-4 transgenic locus and a cognate guide RNA recognition site (CgRRS) in a second DNA junction polynucleotide of the DAS68416-4 transgenic locus.

1b. A transgenic soybean plant cell comprising an INHT27 transgenic locus comprising an insertion and/or substitution of DNA in a DNA junction polynucleotide of a DAS68416-4 transgenic locus with DNA comprising a cognate guide RNA recognition site (CgRRS) or a deletion in a DNA junction polynucleotide of a DAS68416-4 transgenic locus.

2. The transgenic soybean plant cell of embodiment 1a or 1b, wherein said CgRRS comprises the DNA molecule set forth in SEQ ID NO: 8, 9, or 10; and/or wherein said DAS68416-4 transgenic locus is set forth in SEQ ID NO:1, is present in seed deposited at the ATCC under accession No. PTA-10442, is present in progeny thereof, is present in allelic variants thereof, or is present in other variants thereof
3. The transgenic soybean plant cell of embodiments 1a, 1b, or 2, wherein said INHT27 transgenic locus comprises the DNA molecule set forth in SEQ ID NO: 2, 3, 17, or an allelic variant thereof
4. A transgenic soybean plant part comprising the soybean plant cell of any one of embodiments 1a, 1b, 2, or 3, wherein said soybean plant part is optionally a seed.
5. A transgenic soybean plant comprising the soybean plant cell of any one of embodiments 1a, 1b, 2, or 3.
6. A method for obtaining a bulked population of inbred seed comprising selfing the transgenic soybean plant of embodiment 5 and harvesting seed comprising the INHT27 transgenic locus from the selfed soybean plant.
7. A method of obtaining hybrid soybean seed comprising crossing the transgenic soybean plant of embodiment 5 to a second soybean plant which is genetically distinct from the first soybean plant and harvesting seed comprising the INHT27 transgenic locus from the cross.
8. A DNA molecule comprising SEQ ID NO: 2, 3, 8, 9, 10, 11, 16, 17, 23, or an allelic variant thereof
9. A processed transgenic soybean plant product comprising the DNA molecule of embodiment 8.
10. A biological sample containing the DNA molecule of embodiment 8.
11. A nucleic acid molecule adapted for detection of genomic DNA comprising the DNA molecule of embodiment 8, wherein said nucleic acid molecule optionally comprises a detectable label.
12. A method of detecting a soybean plant cell comprising the INHT27 transgenic locus of any one of embodiments 1a, 1b, 2, or 3, comprising the step of detecting DNA molecule comprising SEQ ID NO: 2, 3, 8, 9, 10, 11, 16, 17, 23, or an allelic variant thereof
13. A method of excising the INHT27 transgenic locus from the genome of the soybean plant cell of any one of embodiments 1a, 1b, 2, or 3, comprising the steps of:
(a) contacting the INHT27 transgenic locus comprising the OgRRS and the CgRRS with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and,
(b) selecting a transgenic plant cell, transgenic plant part, or transgenic plant wherein the INHT27 transgenic locus flanked by the OgRRS and the CgRRS has been excised.
14. The method of embodiment 13, wherein said INHT27 transgenic locus comprises the CgRRS of SEQ ID NO: 8, 9, or 10 and the guide RNA comprises an RNA sequence encoded by SEQ ID NO: 13.
15. The method of embodiment 14, wherein said INHT27 transgenic locus comprises the DNA molecule set forth in SEQ ID NO: 3, 17, or an allelic variant thereof.

EXAMPLES

Example 1. Application of a Cas12a RNA Guided Endonuclease and Guide RNAs to Change or Excise the 5'-DNA Junction Sequence in the DAS68416-4 Event The DAS68416-4 5' junction polynucleotide sequence set forth in SEQ ID NO: 1 is flanked by at least three Cas recognition sequences. These can be used to modify some of the 5' junction polynucleotide sequence or eliminate most of it. In one embodiment, Guide RNA-1 (comprising RNA encoded by SEQ ID NO: 4), Guide RNA-2 (comprising RNA encoded by SEQ ID NO: 5), or Guide RNA-3 (comprising RNA encoded by SEQ ID NO: 6) are used alone to disrupt the DAS68416-4 5'-junction sequence (e.g., by using a Cas12a endonuclease and 1 of Guide RNA-1, Guide RNA-2, or Guide RNA-3 to cleave the 5' junction polynucleotide sequence and recovering genomic edits where the 5' DNA junction polynucleotide sequence of DAS68416-4 is disrupted.

The Cas12a nuclease and the single or combined guide RNAs are introduced into soybean plant cells containing the DAS68416-4 event. In certain embodiments, the Cas12a nuclease and gRNA(s) are encoded and expressed from a T-DNA transformed into the DAS68416-4 event via *Agrobacterium*-mediated transformation. Alternatively, the T-DNA can be transformed into any convenient soy line, and then crossed with the DAS68416-4 event to combine the Cas12a ribonucleoprotein expressing T-DNA with the DAS68416-4 event. The Cas12a nuclease and gRNAs can also be assembled in vitro then delivered to DAS68416-4 explants as ribonucleoprotein complexes using a biolistic approach (Svitashev et al., Nat Commun. 2016; 7:13274; Zhang et al., 2021, Plant Commun. 2(2):100168). Also, a plasmid encoding a Cas12a nuclease and the gRNA(s) can be delivered to DAS68416-4 explants using a biolistic approach. This will produce plant cells that have a high likelihood of incurring mutations that disrupt the DAS68416-4 3' junction polynucleotide sequence.

In the *Agrobacterium* approach, a binary vector that contains a strong constitutive expression cassette like the AtUbi10 promoter::AtUbi10 terminator driving Cas12a, a PolII or PolIII gene cassette driving the Cas12a gRNA(s) and a CaMV 35S:NPTII:NOS (i.e., which confers tolerance to G418, kanamycin, and neomycin) or other suitable plant selectable marker (e.g., a phosphomannose isomerase (Reed et al. 2001, *In Vitro Cellular & Developmental Biology—Plant* 37: 127-132) or hygromycin phosphotransferase (Itaya, et al. 2018, *In Vitro Cellular & Developmental Biology—Plant* 54: 184-194)) is constructed and cells comprising the integrated T-DNA(s) are selected using an appropriate selection agent. An expression cassette driving a fluorescent protein like mScarlet may also be useful to monitor the plant transformation process. In the example below, selections for the NPTII marker are provided. It is understood that other selection agents would be used for other selectable markers.

The T-DNA-based expression cassettes are delivered from superbinary vectors in *Agrobacterium* strain LBA4404. Soy transformations are performed based on published methods (e.g., Zhang et al., 1999, Plant Cell, Tissue and Organ Culture 56(1), 37-46) or their equivalents. Briefly, cotyledonary explants are prepared from the 5-day-old soybean seedlings by making a horizontal slice through the hypocotyl region, approximately 3-5 mm below the cotyledon. A subsequent vertical slice is made between the cotyledons, and the embryonic axis is removed. This generates 2 cotyledonary node explants. Approximately 7-12 vertical slices are made on the adaxial surface of the explant about the area encompassing 3 mm above the cotyledon/hypocotyl junction and 1 mm below the cotyledon/hypocotyl junction. Explant manipulations are done with a No. 15 scalpel blade.

Explants are immersed in the *Agrobacterium* inoculum for 30 min and then co-cultured on 100×15 mm Petri plates containing the *Agrobacterium* resuspension medium solidified with 0.5% purified agar (BBL Cat #11853). The co-cultivation plates are overlaid with a piece of Whatman #1 filter paper (Mullins et al., 1990; Janssen and Gardner, 1993; Zhang et al., 1997). The explants (5 per plate) are cultured adaxial side down on the co-cultivation plates, that are overlaid with filter paper, for 3 days at 24° C., under an 18/6 hour light regime with an approximate light intensity of 80 µmol s$^{-1}$ m$^{-2}$ (F17T8/750 cool white bulbs, Litetronics®). The co-cultivation plates are wrapped with Parafilm®. Following the co-cultivation period explants are briefly washed in B5 medium supplemented with 1.67 mg l$^{-1}$ BAP, 3% sucrose, 500 mg l$^{-1}$ ticarcillin and 100 mg l$^{-1}$ cefotaxime. The medium is buffered with 3 mM MES, pH 5.6. Growth regulator, vitamins and antibiotics are filter sterilized post autoclaving. Following the washing step, explants are cultured (5 per plate) in 100×20 mm Petri plates, adaxial side up with the hypocotyl imbedded in the medium, containing the washing medium solidified with 0.8% purified agar (BBL Cat #11853) amended with either G418, neomycin, or kanamycin at concentrations permitting selection of transformants. This medium is referred to as shoot initiation medium (SI). Plates are wrapped with 3M pressure sensitive tape (Scotch™, 3M, USA) and cultured under the environmental conditions used during the seed germination step (at 24° C., 18/6 light regime, under a light intensity of approximately 150 µmol s$^{-1}$ m$^{-2}$.

After 2 weeks of culture, the hypocotyl region is excised from each of the explants, and the remaining explant, cotyledon with differentiating node, is subsequently subcultured onto fresh SI medium. Following an additional 2 weeks of culture on SI medium, the cotyledons are removed from the differentiating node. The differentiating node is subcultured to shoot elongation medium (SE) composed of Murashige and Skoog (MS) (1962) basal salts, B5 vitamins, 1 mg l$^{-1}$ zeatin-riboside, 0.5 mg l$^{-1}$ GA3 and 0.1 mg l$^{-1}$ IAA, 50 mg l$^{-1}$ glutamine, 50 mg l$^{-1}$ asparagine, 3% sucrose and 3 mM MES, pH 5.6. The SE medium is amended with G418, neomycin, or kanamycin at concentrations permitting selection of transformants. The explants are subcultured biweekly to fresh SI medium until shoots reach a length greater than 3 cm. The elongated shoots are rooted on Murashige and Skoog salts with B5 vitamins, 1% sucrose, 0.5 mg l$^{-1}$ NAA without further selection in Magenta Boxes®.

When a sufficient amount of viable tissue is obtained, it can be screened for mutations at the DAS68416-4 junction sequence, using a PCR-based approach. One way to screen is to design DNA oligonucleotide primers that flank and amplify the DAS68416-4 junction plus surrounding sequence. For example, the primers of SEQ ID NO: 14 and SEQ ID NO: 15 will produce an amplification product in a PCR reaction that can be analyzed for edits at the target site. The size of this product will vary based on the nature of the edit. Amplicons can be sequenced directly using an amplicon sequencing approach or ligated to a convenient plasmid vector for Sanger sequencing. Those plants in which the DAS68416-4 5'-junction sequence is disrupted are selected and grown to maturity. The DNA encoding the Cas12a reagents can be segregated away from the modified junction sequence in a subsequent generation. An example of an INHT27 transgenic locus comprising a deletion in a 5' junction polynucleotide which can be produced by using Guide RNA-1 is provided in SEQ ID NO: 2.

Example 2. Introduction of a CgRRS in a 3' Junction Polynucleotide of a DAS68416-4 Transgenic Locus Transgenic plant genomes containing a DAS68416-4 transgenic loci (events) are contacted with:

(i) an ABE or CBE and guide RNAs which recognize the indicated target DNA sites (protospacer (guide RNA coding) plus PAM site) in the 5' or 3' junction polynucleotides of the event to introduce a CgRRS in the junction polynucleotide;
(ii) an RdDe and guide RNAs which recognize the indicated target DNA site (guide RNA coding plus PAM site) in the 5' or 3' junction polynucleotides of the event as well as a donor DNA template spanning the double stranded DNA break site in the junction polynucleotide to introduce a CgRRS in a junction polynucleotide.

Plant cells, callus, parts, or whole plants comprising the introduced CgRRS in the transgenic plant genome are selected.

TABLE 2

Examples of OgRRS and CgRRS in DAS81419

| SOYBEAN EVENT NAME | OgRRS | CgRRS |
| --- | --- | --- |
| DAS68416-4 | (SEQ ID NO: 7; located in 3' junction polynucleotide of SEQ ID NO: 1) | (SEQ ID NO: 8; inserted into 5' junction polynucleotide) |
| | | (SEQ ID NO: 9; inserted into 5' junction polynucleotide) (SEQ ID NO: 10; inserted into 5' junction polynucleotide) |

Example 3. Insertion of a CgRRS Element in the 5'-Junction of the DAS68416-4 Event Two plant gene expression vectors are prepared. Plant expression cassettes for expressing a bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by reference in their entireties. DNA sequences encoding the c2 NLS-Exo, c2 NLS lambda beta SSAP, and c2NLS-SSB fusion proteins are operably linked to suitable promoter(s) (e.g., AtUbi10, CaMV35S, and/or SlUbi10 promoter) and suitable polyadenylation site(s) (e.g., nos 3', PeaE9 3', tmr 3', tms 3', AtUbi10 3', and tr7 3' elements), to provide the exonuclease, SSAP, and SSB plant expression cassettes.

A DNA donor template sequence (SEQ ID NO: 11) that targets the 5' DNA junction polynucleotide of the DAS68416-4 event (SEQ ID NO:1; FIG. 1) for HDR-mediated insertion of a 27 base pair OgRRS sequence (SEQ ID NO: 7) that is identical to a Cas12a recognition site at the 3'-junction polynucleotide of the DAS68416-4 T-DNA insert is constructed. The DNA donor sequence includes a replacement template with desired insertion region (27 base pairs long) flanked on both sides by homology arms about 500-635 bp in length. The homology arms match (i.e., are homologous to) gDNA (genomic DNA) regions flanking the target genomic DNA insertion site (SEQ ID NO: 12) in the DAS68416-4 transgenic locus (SEQ ID NO: 1). The replacement template region comprising the donor DNA is flanked at each end by DNA sequences identical to the DAS68416-4 5' junction polynucleotide sequence and contains a CgRRS element recognized by the same Cas12a RNA-guided nuclease and a gRNA (e.g., comprising an RNA encoded by SEQ ID NO: 13) that recognize the OgRRS of SEQ ID NO: 17 located in the 3' junction polynucleotide.

A plant expression cassette that provides for expression of the RNA-guided sequence-specific Cas12a endonuclease is constructed. A plant expression cassette that provides for expression of a guide RNA (e.g., encoded by SEQ ID NO: 8) complementary to sequences adjacent to the insertion site is constructed. An *Agrobacterium* superbinary plasmid transformation vector containing a cassette that provides for the expression of a suitable plant selectable marker (e.g., a neomycin phosphotransferase (nptII) or hygromycin phosphotransferase (hpt)) is constructed. Once the cassettes, donor sequence and *Agrobacterium* superbinary plasmid transformation vector are constructed, they are combined to generate two soybean transformation plasmids. In other embodiments, other gRNAs (Guide RNA-2 or Guide RNA-3) can be used to introduce double stranded breaks in the DAS68416-4 5' junction polynucleotide for insertion of a CgRRS using similar donor DNA templates and the aforementioned Cas12a, SSAP, SSB, and EXO reagents.

A soybean transformation plasmid is constructed with a neomycin phosphotransferase (nptII) or hygromycin phosphotransferase (hpt) cassette, the RNA-guided sequence-specific endonuclease cassette, the guide RNA cassette, and the DAS68416-4 3'-T_DNA junction sequence DNA donor sequence into the *Agrobacterium* superbinary plasmid transformation vector (the control vector).

A soybean transformation plasmid is constructed with a neomycin phosphotransferase (nptII) or hygromycin phosphotransferase (hpt) cassette, the RNA-guided sequence-specific endonuclease cassette, the guide RNA cassette, the SSB cassette, the lambda beta SSAP cassette, the Exo cassette, and the DAS68416-4 3'-donor DNA template sequence (SEQ ID NO: 11) into the *Agrobacterium* superbinary plasmid transformation vector (the lambda red vector).

All constructs are transformed into *Agrobacterium* strain LBA4404.

Soybean transformations are performed essentially as described in Example 1.

When a sufficient amount of viable tissue is obtained, it can be screened for insertion at the DAS68416-4 junction sequence, using a PCR-based approach. The PCR primer on the 5'-end is set forth in SEQ ID NO: 14. The PCR primer on the 3'-end is—set forth in SEQ ID NO: 15). The above primers that flank donor DNA homology arms are used to amplify the DAS68416-4 5'-junction polynucleotide sequence. The correct donor DNA template sequence insertion will produce a unique PCR product. A unique DNA fragment comprising the CgRRS in the DAS68416-4 5' junction polynucleotide is set forth in SEQ ID NO: 16. Amplicons can be sequenced directly using an amplicon sequencing approach or ligated to a convenient plasmid vector for Sanger sequencing. Those plants in which the DAS68416-4 5' junction sequence now contains the intended Cas12a recognition sequence are selected and grown to maturity. The T-DNA encoding the Cas12a reagents can be segregated away from the modified junction sequence in a subsequent generation. The resultant INHT27 transgenic locus (SEQ ID NO: 17) comprising the CgRRS and OgRRS (e.g., which each comprise SEQ ID NO: 7) can be excised using Cas12a and a suitable gRNA which hybridizes to DNA comprising SEQ ID NO: 13 at both the OgRRS and the CgRRS.

The breadth and scope of the present disclosure should not be limited by any of the above-described embodiments.

What is claimed is:

1. A transgenic soybean plant cell comprising an INHT27 transgenic locus comprising the DNA molecule set forth in SEQ ID NO: 3.

2. A transgenic soybean plant part comprising the soybean plant cell of claim 1.

3. The transgenic soybean plant part of claim 2, wherein said soybean plant part is a seed.

4. A transgenic soybean plant comprising the soybean plant cell of claim 1.

5. A method for obtaining a bulked population of inbred seed comprising selfing the transgenic soybean plant of claim 4 and harvesting seed comprising the INHT27 transgenic locus from the selfed soybean plant.

6. A method of obtaining hybrid soybean seed comprising crossing the transgenic soybean plant of claim 4 to a second soybean plant which is genetically distinct from the first soybean plant and harvesting seed comprising the INHT27 transgenic locus from the cross.

7. A DNA molecule comprising SEQ ID NO: 3.

8. A processed transgenic soybean plant product comprising the DNA molecule of claim 7.

9. A biological sample containing the DNA molecule of claim 7.

10. A method of detecting a soybean plant cell comprising the INHT27 transgenic locus of claim 1, comprising the step of detecting a DNA molecule comprising SEQ ID NO: 9.

11. A method of excising the $INHT_{27}$ transgenic locus from the genome of the soybean plant cell of claim 1, comprising the steps of:
(a) contacting the $INHT_{27}$ transgenic locus of the soybean plant cell with: (i) a $Cas_{12}a$ RNA dependent DNA endonuclease (RdDe); and (ii) a guide RNA (gRNA) capable of hybridizing to the guide RNA hybridization site of the originator guide RNA recognition site (OgRRS) and the cognate guide RNA recognition site (CgRRS) of SEQ ID NO: 3; wherein the $Cas_{12}a$ RdDe recognizes a OgRRS/gRNA and a CgRRS/gRNA hybridization complex; and,
(b) selecting a transgenic plant cell, transgenic plant part, or transgenic plant wherein the $INHT_{27}$ transgenic locus flanked by the OgRRS and the CgRRS has been excised.

12. The method of claim 11, wherein said guide RNA comprises an RNA sequence encoded by SEQ ID NO: 13.

* * * * *

UNITED STATES PATENT AND TRADEMARK OFFICE
CERTIFICATE OF CORRECTION

PATENT NO. : 12,305,175 B2
APPLICATION NO. : 18/057860
DATED : May 20, 2025
INVENTOR(S) : Michael Andreas Kock et al.

It is certified that error appears in the above-identified patent and that said Letters Patent is hereby corrected as shown below:

In the Claims

In Column 70, Claim 11, Line 52:
DELETE "$INHT_{27}$"
INSERT --INHT27--

In Column 70, Claim 11, Line 55:
DELETE "$INHT_{27}$"
INSERT --INHT27--

In Column 70, Claim 11, Line 56:
DELETE "$Cas_{12}a$"
INSERT --Cas12a--

In Column 70, Claim 11, Line 61:
DELETE "$Cas_{12}a$"
INSERT --Cas12a--

In Column 70, Claim 11, Line 65:
DELETE "$INHT_{27}$"
INSERT --INHT27--

Signed and Sealed this
Nineteenth Day of August, 2025

Coke Morgan Stewart
*Acting Director of the United States Patent and Trademark Office*